United States Patent
Ni et al.

(10) Patent No.: US 10,874,616 B2
(45) Date of Patent: *Dec. 29, 2020

(54) SUSTAINED-RELEASE DOSAGE FORMS OF RUXOLITINIB

(71) Applicants: Incyte Corporation, Wilmington, DE (US); Incyte Holdings Corporation, Wilmington, DE (US)

(72) Inventors: Yong Ni, Wilmington, DE (US); Bhavnish Parikh, Avondale, PA (US); Krishnaswamy Yeleswaram, Landenberg, PA (US); Susan Erickson-Viitanen, West Chester, PA (US); William V. Williams, Havertown, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/190,883

(22) Filed: Nov. 14, 2018

(65) Prior Publication Data

US 2019/0231696 A1 Aug. 1, 2019

Related U.S. Application Data

(63) Continuation of application No. 14/079,901, filed on Nov. 14, 2013, now Pat. No. 10,166,191.

(60) Provisional application No. 61/769,408, filed on Feb. 26, 2013, provisional application No. 61/726,893, filed on Nov. 15, 2012.

(51) Int. Cl.
*A61K 9/20* (2006.01)
*A61K 31/519* (2006.01)

(52) U.S. Cl.
CPC .......... *A61K 9/2054* (2013.01); *A61K 31/519* (2013.01)

(58) Field of Classification Search
CPC ...... A61K 31/519; A61K 9/2054; A61P 35/00
See application file for complete search history.

(56) References Cited

U.S. PATENT DOCUMENTS

| | | |
|---|---|---|
| 2,985,589 A | 5/1961 | Broughton et al. |
| 3,832,460 A | 8/1974 | Kosti |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,378,700 A | 1/1995 | Sakuma et al. |
| 5,403,593 A | 4/1995 | Royce |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,153,845 B2 | 12/2006 | Levine |
| 7,167,750 B2 | 1/2007 | Knudson et al. |
| 7,235,258 B1 | 6/2007 | Wells et al. |
| 7,265,108 B2 | 9/2007 | Ozaki |
| 7,335,667 B2 | 2/2008 | Rodgers et al. |
| 7,358,255 B2 | 4/2008 | Nakamura |
| 7,387,793 B2 | 6/2008 | Venkatesh et al. |
| 7,517,870 B2 | 4/2009 | Auricchio |
| 7,544,372 B2 | 6/2009 | Venkatesh et al. |

(Continued)

FOREIGN PATENT DOCUMENTS

| | | |
|---|---|---|
| CN | 102218042 | 10/2011 |
| CN | 102247368 | 11/2011 |

(Continued)

OTHER PUBLICATIONS

Frigols et al., "Pharmaceutical Innovations for the administration of Medicines" Innovaciones Farmacéuticas Para la Administración de Medicamentos, Real Academia de Medicina de la Comunidad Valenciana, dated Jun. 7, 2012, 163 pages (With English Abstract).
Philippine Office Action in Philippine Application No. 1/2015/501089, dated Jul. 1, 2019, 6 pages.
Saffoon et al., "Enhancement of Oral Bioavailability and Solid Dispersion: a Review," J Appl Pharm Sci., 2011, 1(7):13-20.
Thailand Office Action in Thailand Application No. 1501002638, dated Sep. 27, 2019, 2 pages (English Translation).
Costa Rican Office Action in CR Application No. 2015-265, dated Nov. 7, 2019, 16 pages.
Australian Office Action in Argentina Application No. P130104195, dated Sep. 19, 2019, 5 pages.

(Continued)

*Primary Examiner* — Umamaheswari Ramachandran
(74) *Attorney, Agent, or Firm* — Fish & Richardson P.C.

(57) ABSTRACT

The present invention relates to sustained-release formulations and dosage forms of ruxolitinib, or a pharmaceutically acceptable salt thereof, which are useful in the treatment of Janus kinase-associated diseases such as myeloproliferative disorders.

36 Claims, 4 Drawing Sheets

(56) References Cited

U.S. PATENT DOCUMENTS

| | | |
|---|---|---|
| 7,598,257 B2 | 10/2009 | Rodgers et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 | 5/2013 | McAllister |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu et al. |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 10,166,191 B2 | 1/2019 | Ni et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling et al. |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088410 A1 | 4/2009 | Zeldis |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0149825 A1 | 6/2012 | Bandyopadhyay |
| 2012/0214825 A1 | 8/2012 | Vannucchi et al. |
| 2012/0225057 A1 | 9/2012 | Flynn |
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |

(56) References Cited

U.S. PATENT DOCUMENTS

| | | |
|---|---|---|
| 2014/0303196 A1 | 10/2014 | Rodgers et al. |
| 2014/0343030 A1 | 11/2014 | Li et al. |
| 2015/0065447 A1 | 3/2015 | Sander |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons |
| 2015/0164900 A1 | 6/2015 | Rodgers et al. |
| 2015/0225412 A1 | 8/2015 | Brameld |
| 2015/0246046 A1 | 9/2015 | Vaddi |

FOREIGN PATENT DOCUMENTS

| | | |
|---|---|---|
| CN | 102772384 | 11/2012 |
| DE | 30 36 390 | 5/1982 |
| EA | 201590272 | 5/2015 |
| EP | 0223420 | 5/1987 |
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |
| JP | 2003/155285 | 5/2003 |
| JP | 2006/518341 | 8/2006 |
| WO | WO 96/030343 | 10/1996 |
| WO | WO 97/002262 | 1/1997 |
| WO | WO 97/002266 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 01/014402 | 3/2001 |
| WO | WO 01/027104 | 4/2001 |
| WO | WO 01/042246 | 6/2001 |
| WO | WO 01/064655 | 9/2001 |
| WO | WO 01/081345 | 11/2001 |
| WO | WO 01/098344 | 12/2001 |
| WO | WO 02/000196 | 1/2002 |
| WO | WO 02/000661 | 1/2002 |
| WO | WO 02/016370 | 2/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/088952 | 10/2003 |
| WO | WO 03/092595 | 11/2003 |
| WO | WO 03/099771 | 12/2003 |
| WO | WO 03/099796 | 12/2003 |
| WO | WO 04/003026 | 1/2004 |
| WO | WO 04/005281 | 1/2004 |
| WO | WO 04/005282 | 1/2004 |
| WO | WO 04/026406 | 4/2004 |
| WO | WO 04/041814 | 5/2004 |
| WO | WO 04/046120 | 6/2004 |
| WO | WO 04/047843 | 6/2004 |
| WO | WO 04/056786 | 7/2004 |
| WO | WO 04/072063 | 8/2004 |
| WO | WO 04/080980 | 9/2004 |
| WO | WO 04/092154 | 10/2004 |
| WO | WO 04/099204 | 11/2004 |
| WO | WO 04/099205 | 11/2004 |
| WO | WO 05/005988 | 1/2005 |
| WO | WO 05/013986 | 2/2005 |
| WO | WO 05/020921 | 3/2005 |
| WO | WO 05/026129 | 3/2005 |
| WO | WO 05/028444 | 3/2005 |
| WO | WO 05/049033 | 6/2005 |
| WO | WO 05/051393 | 6/2005 |
| WO | WO 05/060972 | 7/2005 |
| WO | WO 05/061463 | 7/2005 |
| WO | WO 05/062795 | 7/2005 |
| WO | WO 05/089502 | 9/2005 |
| WO | WO 05/095400 | 10/2005 |
| WO | WO 05/105146 | 11/2005 |
| WO | WO 05/105814 | 11/2005 |
| WO | WO 05/105988 | 11/2005 |
| WO | WO 05/110410 | 11/2005 |
| WO | WO 05/117909 | 12/2005 |
| WO | WO 05/121130 | 12/2005 |
| WO | WO 05/123719 | 12/2005 |
| WO | WO 06/004984 | 1/2006 |
| WO | WO 06/013114 | 2/2006 |
| WO | WO 06/022459 | 3/2006 |
| WO | WO 06/039718 | 4/2006 |
| WO | WO 06/046023 | 5/2006 |
| WO | WO 06/046024 | 5/2006 |
| WO | WO 06/052913 | 5/2006 |
| WO | WO 06/056399 | 6/2006 |
| WO | WO 06/067445 | 6/2006 |
| WO | WO 06/069080 | 6/2006 |
| WO | WO 06/077499 | 7/2006 |
| WO | WO 06/096270 | 9/2006 |
| WO | WO 06/101783 | 9/2006 |
| WO | WO 06/108103 | 10/2006 |
| WO | WO 06/122806 | 11/2006 |
| WO | WO 06/127587 | 11/2006 |
| WO | WO 06/129199 | 12/2006 |
| WO | WO 06/136823 | 12/2006 |
| WO | WO 07/002433 | 1/2007 |
| WO | WO 07/025090 | 3/2007 |
| WO | WO 07/041130 | 4/2007 |
| WO | WO 07/043677 | 4/2007 |
| WO | WO 07/044894 | 4/2007 |
| WO | WO 07/049041 | 5/2007 |
| WO | WO 07/062459 | 6/2007 |
| WO | WO 07/070514 | 6/2007 |
| WO | WO 07/076423 | 7/2007 |
| WO | WO 07/077949 | 7/2007 |
| WO | WO 07/080766 | 7/2007 |
| WO | WO 07/084557 | 7/2007 |
| WO | WO 07/090141 | 8/2007 |
| WO | WO 07/090748 | 8/2007 |
| WO | WO 07/116313 | 10/2007 |
| WO | WO 07/117494 | 10/2007 |
| WO | WO 07/129195 | 11/2007 |
| WO | WO 07/135461 | 11/2007 |
| WO | WO 07/140222 | 12/2007 |
| WO | WO 07/143155 | 12/2007 |
| WO | WO 08/013925 | 1/2008 |
| WO | WO 08/028937 | 3/2008 |
| WO | WO 08/035376 | 3/2008 |
| WO | WO 08/043031 | 4/2008 |
| WO | WO 08/058126 | 5/2008 |
| WO | WO 08/064157 | 5/2008 |
| WO | WO 08/067119 | 6/2008 |
| WO | WO 08/077712 | 7/2008 |
| WO | WO 08/079291 | 7/2008 |
| WO | WO 08/079292 | 7/2008 |
| WO | WO 08/082198 | 7/2008 |
| WO | WO 08/082839 | 7/2008 |
| WO | WO 08/082840 | 7/2008 |
| WO | WO 08/106692 | 9/2008 |
| WO | WO 08/124323 | 10/2008 |
| WO | WO 08/139161 | 11/2008 |
| WO | WO 08/145681 | 12/2008 |
| WO | WO 08/145688 | 12/2008 |
| WO | WO 08/157207 | 12/2008 |

(56) References Cited

FOREIGN PATENT DOCUMENTS

| | | |
|---|---|---|
| WO | WO 08/157208 | 12/2008 |
| WO | WO 09/007839 | 1/2009 |
| WO | WO 09/016460 | 2/2009 |
| WO | WO 09/049028 | 4/2009 |
| WO | WO 09/064486 | 5/2009 |
| WO | WO 09/064835 | 5/2009 |
| WO | WO 09/071577 | 6/2009 |
| WO | WO 09/100130 | 8/2009 |
| WO | WO 09/109576 | 9/2009 |
| WO | WO 09/114512 | 9/2009 |
| WO | WO 09/115572 | 9/2009 |
| WO | WO 09/155156 | 12/2009 |
| WO | WO 09/158687 | 12/2009 |
| WO | WO 10/000978 | 1/2010 |
| WO | WO 10/001169 | 1/2010 |
| WO | WO 10/020905 | 2/2010 |
| WO | WO 10/022076 | 2/2010 |
| WO | WO 10/022081 | 2/2010 |
| WO | WO 10/026121 | 3/2010 |
| WO | WO 10/026122 | 3/2010 |
| WO | WO 10/026124 | 3/2010 |
| WO | WO 10/039939 | 4/2010 |
| WO | WO 10/081692 | 7/2010 |
| WO | WO 10/083283 | 7/2010 |
| WO | WO 10/135621 | 11/2010 |
| WO | WO 10/135650 | 11/2010 |
| WO | WO 11/003418 | 1/2011 |
| WO | WO 11/025685 | 3/2011 |
| WO | WO 11/028685 | 3/2011 |
| WO | WO 11/029802 | 3/2011 |
| WO | WO 11/031554 | 3/2011 |
| WO | WO 11/035900 | 3/2011 |
| WO | WO 11/044481 | 4/2011 |
| WO | WO 11/057784 | 5/2011 |
| WO | WO 11/069141 | 6/2011 |
| WO | WO 2011/066369 | 6/2011 |
| WO | WO 11/112662 | 9/2011 |
| WO | WO 11/130146 | 10/2011 |
| WO | WO 11/144338 | 11/2011 |
| WO | WO 11/146808 | 11/2011 |
| WO | WO 12/003457 | 1/2012 |
| WO | WO 2012/045010 | 4/2012 |
| WO | WO 12/068440 | 5/2012 |
| WO | WO 12/068450 | 5/2012 |
| WO | WO 12/177606 | 12/2012 |
| WO | WO 13/007765 | 1/2013 |
| WO | WO 13/007768 | 1/2013 |
| WO | WO 13/023119 | 2/2013 |
| WO | WO 13/026025 | 2/2013 |
| WO | WO 13/036611 | 3/2013 |
| WO | WO 13/173720 | 11/2013 |
| WO | WO 2014/016396 | * 1/2014 |
| WO | WO 14/071031 | 5/2014 |
| WO | WO 14/138168 | 9/2014 |

OTHER PUBLICATIONS

Australian Office Action in Australian Application No. 2018203899, dated Jan. 21, 2020, 5 pages.
Australian Office Action in Australian Application No. 2018203899, dated Feb. 12, 2020, 5 pages.
Canadian Office Action in Canadian Application No. 2,890,755, dated Oct. 8, 2019, 3 pages.
Eurasian Office Action in Eurasian Application No. 201590930, dated Feb. 10, 2020, 10 pages.
Japanese Office Action in Japanese Application No. 2019-039497, dated Feb. 18, 2020, 9 pages.
Mexican Office Action in Mexican Application No. MX/a.2015/005947, dated Nov. 28, 2019, 6 pages.
Sri Lanka Office Action in Sri Lanka Application No. 18230, dated Dec. 16, 2019, 1 page.
Taiwan Office Action in Taiwan Application No. 107133083, dated Nov. 11, 2019, 11 pages.
Taiwan Office Action in Taiwan Application No. 102141524, dated Oct. 8, 2019, 5 pages.
Orlando et al., "Melkersson-Rosenthal syndrome," Arch Otolaryngol Head Neck Surg., Jun. 1990, 116(6):728-729.
Shilling et al., "Metabolism, excretion, and pharmacokinetics of [14C]INCB018424, a selective Janus tyrosine kinase 1/2 inhibitor, in humans," Drug Metab Dispos., Nov. 2010, 38(11):2023-2031.
Peruvian Office Action in Peruvian Application No. 624-2015, dated May 21, 2019, 13 pages.
Colombian Office Action in Colombian Application No. 15-114.028, dated May 10, 2019, 4 pages.
Costa Rican Office Action in CR Application No. 2015-265, dated May 27, 2019, 13 pages.
European Communication in European Application No. 13798840.8, dated Jul. 24, 2019, 4 pages.
Israeli Office Action in Israeli Application No. 238,765, dated Jul. 23, 2019, 7 pages.
No Author, "Hypromellose," last updated Apr. 10, 2019, [date retrieved Jul. 23, 2019] retrieved from URL <https://en.wikipedia.org/wiki/Hypromellose>, 3 pages.
Indonesian Office Action in Indonesian Application No. P00201503544, dated Jun. 21, 2019, 3 pages.
New Zealand Office Action in New Zealand Application No. 748448, dated Jul. 11, 2019, 3 pages.
New Zealand Office Action in New Zealand Application No. 708157, dated May 2, 2019, 3 pages.
Mexican Office Action in Mexican Application No. MX/a.2015/005947, dated Apr. 24, 2019, 5 pages.
ClinicalTrials.gov, "History of Changes for Study: NCT01340651 Study of Ruxolitinib (INCB018424) Sustained Release Formulation in Myelofibrosis Patients," Feb. 5, 2014, [retrieved on May 10, 2019] retrieved from URL <https://clinicaltrials.gov/ct2/history/NCT01340651>, 2 pages.
U.S. Appl. No. 14/263,476, filed Apr. 28, 2014, Rodgers et al.
U.S. Appl. No. 14/593,688, 14/593,688, Zhou et al.
U.S. Appl. No. 14/633,605, filed Feb. 27, 2015, Vaddi.
U.S. Appl. No. 14/697,236, filed Apr. 27, 2015, Yao et al.
U.S. Appl. No. 14/699,500, filed Apr. 29, 2015, Zhou et al.
U.S. Appl. No. 14/711,576, filed May 13, 2015, Rodgers et al.
U.S. Appl. No. 14/714,820, filed May 18, 2015, Parikh et al.
U.S. Appl. No. 14/799,777, filed Jul. 15, 2015, Rodgers et al.
"FDA prescribing information for Jakafi (Ruxolitinib dosage form)", (Nov. 1, 2011) Retrieved from the Internet: URL: http://www.accessdata.fda.gov/drugsatfda_docs/labels/2011/202192lb1.pdf [retrieved on Sep. 25, 2013] 22 pages.
26th Annual JPMorgan Healthcare Conference presentation dated Jan. 8, 2008 (28 pages).
Abe, et al., Heterocycles, "Effective Methods for Introducing Some Aryl and Heteroaryl Substituent onto 1-Azaazulene Nuclei", 66, 229-240 (2005).
Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002; 506:1079-86)
Abstract of Chilean patent application No. 3496-06 published in Official Gazette of the Republic of Chile (Jun. 1, 2007) and publication (2 pages).
Aho, T. et al., Expression of human pim family genes is selectively up-regulated by cytokines promoting T helper type 1, but not T helper type 2, cell differentiation, Immunology, 116: 82-88, 2005.
Albach et al., "Diagnosis of keratoconjunctivitis sicca in rheumatoid arthritis. The value of various tests", Ophthalmologe, Apr. 1994; 91(2):229-34—in German (with English abstract/summary contained therein).
Anderson et al., "Biochemical characterization of GSK1070916, a potent and selective inhibitor of Aurora B and Aurora C kinases with an extremely long residence time", Biochem. J., 420(2), 259-265 (2009).

(56) References Cited

OTHER PUBLICATIONS

Australian Office Action in Australian Application No. 2013344780, dated May 5, 2017, 4 pages.
Australian Office Action in Australian Application No. 201803899, dated Feb. 14, 2019, 5 pages.
Bachmann, et al., "The serine/threonine kinease Pim-1," The International Journal of Biochechemistry and Cell Biology 37: 726-730 (2005).
Banker, et al., "Modern Pharmaceuticals" p. 596 (1996).
Barabino et al., "Tear film and ocular surface tests in animal models of dry eye; uses and limitations", Experimental Eye Research, 2004, 79, 613-621.
Barr et al., "Corneal scarring in the Collaborative Longitudinal Evaluation of Keratoconus (CLEK) Study: baseline prevalence and repeatability of detection", Cornea, 1999; 18(1):34-46.
Baudouin et al., "Flow cytometry in impression cytology specimens. A new method for evaluation of conjunctival Inflammation", Invest Ophthalmol Vis Sci, 1997; 38:1458-1464.
Baxter et al., "Reductive Aminations of Carbonyl Compounds with Borohydride and Borane Reducing Agents," Organic Reactions, 2002, 1-57.
Baytel et al., "The human Pim-2 proto-oncogene and its testicular expression" Biochimica et Biophysica Acta 1442: 274-285, (1998).
Beck et al., "Brief Report: Alleviation of Systemic Manifestations of Castleman's Disease by Monoclonal Anti-Interleukin-6 Antibody," *N. Engl. J. Med.,* 1994, 330(9):602-605.
Begley, et al., "Use of the dry eye questionnaire to measure symptoms of ocular irritation in patients with aqueous tear deficient dry eye", Cornea, 2002:21:664-70.
Bell, Malcolm, and Zalay, Andrew, "Synthesis of Substituted 3-Amino[6,5-b] triazinoindoles." Journal of Heterocyclic Chemistry, 12(5):1001-1004, Oct. 1975.
Bennett et al., "Proposals for the classification of the myelodysplastic syndromes," British Journal of Haematology, 1982, 51: 189-199.
Berge, et al., "Pharmaceutical salts", J. Pharma. Science (1977) vol. 66(1) pp. 1-19.
Beyer, "Uber die Synthese von 2-Methylmercapto-1.3.4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhattacharya et al., "Brittain, ed. Polymorphism in Pharmaceutical Solids," 2009, p. 327-345.
Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.
Bioreversible Carriers in Drug Design, ed. Edward B. Roche, American Pharmaceutical Association and Pergamon Press, 1987* too voluminous to provide.
Blume-Jensen, et al, "Oncogenic kinase signaling", Nature 2001, 411(6835):355-365.
Bock, C., et al. "Managing drug resistance in cancer: lessons from HIV therapy." Nature. (Jul. 2012), vol. 12, pp. 494-501.
Bolen, "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).
Borie, et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.
Bosworth, "JAK1/JAK2 Inhibitor Ruxolitinib Is a Rising Start," Clinical Oncology, Apr. 2011, vol. 06:04, 3 pages.
Boudny, et al., "JAK/STAT signaling pathways and cancer" Neoplasm, 49:349-355, 2002.
Bourcier et al., "Expression of CD40 and CD40 ligand in the human conjunctival epithelium", Invest Ophthalmol Vis Sci, 2000;41:120-126.
Bowman, et al. "STATs in oncogenesis", Oncogene, 19:2474-2488, 2000.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998:67:687-697.
Brignole et al., "Flow cytometric analysis of inflammatory markers in conjunctival epithelial cells of patients with dry eyes", Invest Ophthalmol Vis Sci, 2000; 41:1356-1363.
Brignole et al., "Flow cytometric analysis of inflammatory markers in KCS: 6-month treatment with topical cyclosporin A", Invest Ophthalmol Vis Sci, 2001; 42:90-95.
Brignole et al., "Flow cytometry in conjunctival impression cytology: a new tool for exploring ocular surface pathologies", Exp Eye Res, 2004;78:473-481.
Bromberg et al., "Inflammation and Cancer: IL-6 and STAT3 Complete the Link," Cancer Cell, 15:79-80 (2009).
Bron, et al., "Grading of corneal and conjunctival staining in the context of other dry eye tests", Cornea, 2003;22(7):640-50.
Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).
Bunning and Germing, "Myelodysplastic syndromes/neoplasms" in Chapter 5, Swerdlow, et al, eds. WHO Classification of Tumours of Haematopoietic and Lymphoid Tissues, (ed. 4th edition): Lyon, France: IARC Press;2008:88-103.
Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.
Burger et al., "Gp130 and ras mediated signaling in human plasma cell line IN/a-6: a cytokine-regulated tumor model for plasmacytoma", Hematol J., 2:42-53, 2001.
Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, et al. (2002). "Molecular aspects of primary immuno-deficiencies: lessons from cytokine and other signaling pathways.", J Clin Invest, 109(10): 1261-9.
Candotti, F., et al. (1997). "Structural and functional basis for JAK3-deficient severe combined immunodeficiency.", Blood, 90(10): 3996-4003.
Carey and Sundberg, Advanced Organic Chemistry, Part B: Reactions and Synthesis, 4th ed., Kluwer Academic/Plenum Publishers:New York, pp. 111-119 (2001).
Carey and Sundberg, Advanced Organic Chemistry, Part B: Reactions and Synthesis, Oxidations, 4th ed., Kluwer Academic/Plenum Publishers:New York, pp. 747-757 (2001).
Cermak, et al, "Is complete androgen insensitivity syndrome associated with alterations in the meibomium gland and ocular surface", Cornea, 2003;22:516-521.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia,* 2013, 13(3):333-337.
Chauhan and Patel, "A concise review on sustained drug delivery system and its opportunities," Am J Pharmtech Res., Mar. 2012, 2(2), 12 pages.
Chauhan et al., "A concise review on sustained drug delivery system and its opportunities," International Journal on Pharmtech Research, Mar. 2012, 2: 227-238.

(56) References Cited

OTHER PUBLICATIONS

Chauhan, et al, "Autoimmunity in Dry Eye due to resistance of Th17 to Treg Suppression", J. Immunology, 182(3):1247-52 (2009).
Chemical encyclopedia, vol. 1, pp. 242-243, publication "Soviet Encyclopedia," Moscow, 1988.
Chen et al., "Induction of myelodysplasia by myeloid-derived suppressor cells," J Clin Invest, Nov. 2013, 123(11): 4595-611.
Chen et al., "Blockade of interleukin-6 signaling augments regulatory T-cell reconstitution and attenuates the severity of graft-versus-host disease," Blood, Jul. 2009, 114(4): 891-900.
Chen, et al., "STAT3 Activation in Human Endometrial and Cervical Cancer", British Journal of Cancer, 96, 591-599, 2007.
Cheson et al., "Report of an international working group to standardize response criteria for myelodysplastic syndromes," Blood, Dec. 2000, 96(12): 3671-4.
Chew, et al., "An instrument for quantifying meibomian lipid on the lid margin: the Meibometer", Curr Eye Res, 1993a;12:247-254.
Chew, et al., "The casual level of meibomian lipids in humans", Current Eye Research, 1993b;12:255-259.
Chinese Office Action in Chinese Application No. 201380070296.8, dated Feb. 16, 2017, 19 pages (with English translation).
Chinese Office Action in Chinese Application No. 201380070296.8, dated Sep. 30, 2018, 8 pages.
Cho, et al, "Review of the tear break-up time and a closer look at the tear break-up time of Hong Kong Chinese", Optom Vis Sci, 1993;70(1):30-8.
Choi Ha-Soon, et al, "Design and synthesis of 7H-pyrrolo[2,3-d]pyrimidines as focal adhesion kinase inhibitors. Part 1", Bioorg. & Med. Chem. Lett., 16(8):2173-2176 (2006).
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Chu-Moyer, et al., "Preparation of the Pour Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Claessens et al., "In vitro proliferation and differentitation of erythyroid progenitors from patients with myelodysplastic syndromes: evidence for Fas-dependent apoptosis," Blood, Mar. 2012, 1594-1601.
Claridge et al., "Discovery of a novel and potent series of thieno[3,2-b]pyridine-based inhibitors of c-Met and VEGFR2 tyrosine kinases," Bioorganic Medicinal Chemistry Letters, 2008, 2793-2798.
Clark et al., "Discovery and Development of Janus Kinase (JAK) inhibitors for Inflammatory Diseases," J Med Chem., 2014, pp. A-P.
Coligan, J.E. et al, Wiley Press; Methods in Molecular Biology: vol. 225, Inflammation Protocols., Winyard, P.G. and Willoughby, D.A., Humana Press (2003)* too voluminous to provide.
Columbian Office Action in Columbian Application No. 15-114.028, dated Apr. 18, 2017, 6 pages.
Columbian Office Action in Columbian Application No. 15-114.028, dated Sep. 20, 2017, 8 pages.
Communication dated Jan. 22, 2009 for European Appln. No. 06839328.9 (5 pgs.).
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.

Current Protocols in Immunology, vol. 3., Coligan, J.E. et al, Wiley Press (1988)* too voluminous to provide.
Daniels et al., "Imatinib mesylate inhibits the profibrogenic activity of TGF—? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol. 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deisseroth et al.,"U.S. Food and Drug Administration Approval: Ruxolitinib for the Treatment of Patients with Intermediate and High-Risk Myelofibrosis," Clin. Cancer Res., Jun. 2012, 18(12):3212-3217.
Deng Jun, et al, "Rh-catalyzed asymmetric hydrogenation of gamma-phthalimido-substituted esters: an efficient enantioselective synthesis of beta-aryl-gamma-amino acids", Org. Lett. 9(23):4825-4827 (2007).
Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7-dihydro[1.2.4]triazino[1,6-c]quinazolin-5-ium-1-olates", Tetrahedron, 30:3997-4012, 1974.
Dorwald: "Side Reactions in Organic Synthesis: A Guide to Successful Synthesis Design" 2005 Wiley-VCH Verlag GmbH & Co. KGaA, Wienheim, chapter 1, 32 pages.
Dudley, A.C., et al. "AVEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract poster.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Eurasian Office Action in Eurasian Application No. 201590930, dated Apr. 5, 2016, 6 pages (English Translation).
European Communication in European Application No. 13798840.8, dated May 11, 2018, 5 pages.
Expert Scientific Group on Phase One Clinical Trials Final Report, Nov. 30, 2006, pp. C1, C35-C38.
Fabrizio Saettone, "Ocular inserts for topical delivery", Advanced Drug Delivery Reviews 16:95-106 (1998).
Farrell et al., "A classification for dry eyes following comparison of tear thinning time with Schirmer tear test", Acta Ophthalmol (Copenh), 1992; 70(3):357-60.
Farrell et al., "A clinical procedure to predict the value of temporary occlusion therapy in keratoconjunctivitis sicca" Ophthal Physiol Opt, 2003;23:1-8.
Farris, "Tear osmolarity—a new gold standard?" Adv Exp Med Biol, 350:495-503, 1994.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux et al., "Efficacy of azacitidine compared with that of conventional care regimens in the treatment of higher-risk myelodysplastic syndromes: a randomised, open-label, phase III study," Lancet Oncol, Mar. 2009, 10:223-32.

(56) References Cited

OTHER PUBLICATIONS

Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications: vol. 116, No. 21 Nov. 1, 2010 p. 349, XP002667216. ISSN: 0002-7863 (1 page).
Flex E., et al., "Somatically acquired JAK1 mutations in adult acute lymphoblastic leukemia", J. Exp Med. 205:751-8, (2008).
Fonseca, J.E. et al., "Interleukin-6 as a key player in systemic inflammation and joint destruction", Autoimmunity Reviews, 8:538-42, (2009).
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Absract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007(1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY, Nov. 8-10, 2007. Poster 0009 (1 page).
Fujihara et al., "Evaluation of human conjunctival epithelium by a combination of brush cytology and flow cytometry: an approach to the quantitative technique", Diagn Cytopathol. 1997;17:456-60.
Fujii, C. et al., "Aberrant expression of serine.threeonine kinase Pim-3 in hepatocellular carcinoma development and its role in the proliferation of human hepatoma cell lines" International Journal of Cancer 114: 209-218, (2005).
Fukagawa et al., "Histological evaluation of brush cytology of rabbit conjunctiva", Nippon Ganka Gakkai Zasshi, 1993;97:1173-8 (contains English abstract within the article).
Gaertner, "Cyclization of l-Alkylamino-3-halo-2-alkanolst o l-Alkyl-3-azetidinols," J. Org. Chem., 1967, 32, 2972-76.
Gaestel et al., "Targeting innate immunity protein kinase signalling in inflammation," Nat Rev Drug Discov., Jun. 2009, 8(6):480-99.
Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 48:3396-3401 (2004).
Gilchrist et al., "5H-2-Pyrindines from 2-Bromocyclopentene-l-carboxaldehyde," Tetrahedron, Jan. 1, 1995, pp. 9119-9126.
Glasson et al., "Differences in clinical parameters and tear film of tolerant and intolerant contact lens wearers", Invest Ophthalmol Vis Sci, 2003;44:5116-5124.
Glaitfeld, "Improvements in the Preparation of DL-Threonic and DL-Erythronic Acids", J. Am. Chem. Soc. 62:974-977 (1940).

Gobbels et al., Tear secretion in dry eyes as assessed by objective fluorophotometry. Ger J Ophthalmol, 1992; 1:350-353.
Golding et al., "X-ray and scanning electron microscopic analysis of the structural composition of tear ferns", Cornea Jan. 1994;13(1):58-66.
Gomtsyan, et al, "Design, synthesis, and structure-activity relationship of 6-alkynylpyrimidines as potent adenosine kinase inhibitors", J. Med. Chem. 45(17):3639-3648 (2002).
Goodman, et al., "IL-6 Signaling in Psoriasis Prevents Immune Suppression by Regulatory T Cells," J. Immunol., Sep. 2009, 183: 3170-3176.
Gooseman, et al., "The intramolecular b-fluorine . . . ammonium interaction in 4- and 8-membered rings", Chem. Commun, vol. 30, pp. 3190-3192 (2006).
Gorr et al., "Clinical Resistance to STI-571 Cancer Therapy Caused by BCR-ABL Gene Mutation or Amplification." Science, 293:876, 2001.
Gorre, M.E., et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303 (12 pp.).
Goto et al., Color mapping of tear lipid layer thickness distribution from the image analysis in DR-1 tear lipid layer interference images (ARVO abstract), ARVO 2004.
Goto et al., "Computer-synthesis of an interference color chart of human tear lipid layer by a colorimetric approach",Invest Ophthalmol Vis Sci, 2003;44:4693-7.
Goto et al., "Differentiation of lipid tear deficiency dry eye by kinetic analysis of tear interference images", Arch Ophthalmol, 2003;121:173-80.
Goto et al., "Evaluation of the tear film stability after laser in situ keratomileusis using the tear film stability analysis system", Am J Ophthalmol, 2004b Jan.;137(1):116-20.
Goto et al., "Tear Film Stability Analysis System: Introducing a new application for videokeratography", Cornea, 2004a; Nov.;23(8):S65-S70.
Goto, et al., Kinetic analysis of tear interference images in aqueous tear deficiency dry eye before and after punctal occlusion. Invest Ophthalmol Vis Sci, 2003;44:1897-905.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic—contact hypersensitivity", Immunol Today, Jan.; 19(1):37-44 (1998) (only 1 page provide and marked "best available copy").
Green, T.W. and Wuts, P.G.M.. Protective Groups in Organic Synthesis, 3rd. Ed., Wiley & Sons, Inc., New York (1999)* too voluminous to provide.
Greenberg, "The Role of Hemopoietic Growth Factors in the Treatment of Myelodysplastic Syndromes," International Journal of Pediatrick Hematology, 4(3): 231-238.
Greenberg, "The myelodysplastic syndromes" in Hoffman, et al, eds. Hematology: Basic Principles and Practice (3rd ed.), Churchill Livingston; 2000:1106-1129.
Greene et al., Greene's Protective Groups in Organic Synthesis, 2007, 4th Edition, 54-55.
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Guillon, Jean-Pierre, "Tear film photography and contact lens wear", J Br Contact Lens Assoc, 1982;5:84-7.

(56) References Cited

OTHER PUBLICATIONS

Gura, "Systems for Identifying New Drugs Are Often Faulty," Science, Nov. 1997, 278(5340): 1041-1042.
Guschin, et al, "A major role for the protein tyrosine kinase JAK1 in the JAK1STAT signal transduction pathway in response to interleukin-6", Embo J 14:1421-1429 (1995).
Hamze et al., "Synthesis of Various 3-Substituted 1,2,4-Oxadiazole-Containing Chiral β3—and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.
Harrison et al., "JAK Inhibition with Ruxolitinib versus Best Available Therapy for Myelofibrosis," The New England Journal of Medicine, Mar. 2012, 366(9): 787-798.
Helal et al., "Stereoselective Synthesis of cis-1,3-Disubstituted Cyclobutyl Kinase Inhibitors," Organic Letters, (2004), 6(11), pp. 1853-1856.
Hickenbottom "Reactions of organic compounds," State Scientific-Technical Publishing Association, Chemical Literature Section, Moscow, 1939, pp. 360-362.
Higuchi, et al., "Pro-drugs as Novel Delivery Systems," vol. 14 of the A.C.S. Symposium Series (1975)* too voluminous to provide.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
Hyung-Bae et al., "CP-690550, a Janus Kinase Inhibitor, Suppresses CD4+ T-Cell-Mediated Acute Graft-Versus-Host Disease by Inhibiting the Interferon-Y Pathway," *Transplantation*, 2010, 90(8):825-835.
Indian Office Action in Indian Application No. 5153/DELNP/2015, dated Jan. 31, 2019, 6 pages.
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 dated Dec. 17, 2009 (7 pages).
International Preliminary Report on Patentability for PCT/US2009/036635 dated Sep. 14, 2010 (6 pages).
International Preliminary Report on Patentability for PCT/US2009/059203 dated Apr. 5, 2011 (6 pages).
International Preliminary Report on Patentability for PCT/US2010/021003 dated Jul. 19, 2011 (11 pages).
International Preliminary Report on Patentability for PCT/US2010/052011 dated Apr. 11, 2012 (4 pages).
International Preliminary Report on Patentability for PCT/US2011/025433 dated Aug. 21, 2012 (7 pages).
International Preliminary Report on Patentability for PCT/US2011/027665 dated Sep. 11, 2012 (7 pages).
International Preliminary Report on Patentability for PCT/US2011/037291 dated Nov. 27, 2012 (7 pages).
International Preliminary Report on Patentability for PCT/US2011/061351 dated May 30, 2013 (7 pages).
International Preliminary Report on Patentability for PCT/US2011/061374 dated May 30, 2013 (5 pages).
International Preliminary Report on Patentability for PCT/US2012/043099 dated Dec. 23, 2013, 6 pages.
International Preliminary Report on Patentability for PCT/US2012/050210 dated Feb. 11, 2014, 8 pages.
International Preliminary Report on Patentability for PCT/US2012/051439 dated Feb. 27, 2014, 7 pages.
International Preliminary Report on Patentability for PCT/US2012/053921 dated Mar. 20, 2014, 8 pages.
International Preliminary Report on Patentability for PCT/US2013/041601, dated Nov. 18, 2014, 7 pages.
International Preliminary Report on Patentability for PCT/US2013/070012, dated May 28, 2015, 8 pages.
International Search Report and the Written Opinion, PCT/US2012/051439, dated Nov. 30, 2012 (15 pages).
International Search Report and the Written Opinion, PCT/US2012/053921, dated Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pgs.).
International Search Report and Written Opinion for International Appln. No. PCT/US2009/036635 dated Jun. 3, 2009 14 pages.
International Search Report and Written Opinion for PCT/US2006/047369, 16 pages (dated Apr. 24, 2007).
International Search Report and Written Opinion for PCT/US2008/083319, 29 pages dated Mar. 13, 2009.
International Search Report and Written Opinion for PCT/US2011/025433, 12 pages (dated Jul. 20, 2011).
International Search Report and Written Opinion for PCT/US2011/027665 dated Jun. 27, 2011 (14 pages).
International Search Report and Written Opinion for PCT/US2011/037291, 11 pages (dated Apr. 19, 2012).
International Search Report and Written Opinion for PCT/US2011/061351 dated Feb. 17, 2012 (12 pages).
International Search Report and Written Opinion for PCT/US2011/061374 dated Mar. 27, 2012 (10 pages).
International Search Report and Written Opinion for PCT/US2012/025581, 16 pages (dated Apr. 26, 2011).
International Search Report and Written Opinion for PCT/US2012/025581, 16 pages (dated Apr. 26, 2012).
International Search Report and Written Opinion for PCT/US2012/043099, 11 pages dated Sep. 13, 2012.
International Search Report and Written Opinion for PCT/US2012/050252 dated Jan. 2, 2013, 17 pages.
International Search Report and Written Opinion in International Application No. PCT/US2013/067794, dated Dec. 17, 2013, 14 pages.
International Search Report and Written Opinion in International Application No. PCT/US2013/070012, dated Jan. 23, 2014, 12 pages.
International Search Report and Written Opinion in International Application No. PCT/US2014/020554, dated Jul. 16, 2014, 17 pages.
International Search Report and Written Opinion in International Application No. PCT/US2014/049940, dated Nov. 4, 2014, 13 pages.
International Search Report and Written Opinion in International Application No. PCT/US2014/051678, dated Feb. 11, 2015, 22 pages.
International Search Report for PCT/US2008/66658 dated Dec. 23, 2008 (4 pages).
International Search Report for PCT/US2010/021003 dated Aug. 16, 2010 (8 pages).

(56) References Cited

OTHER PUBLICATIONS

International Search Report for PCT/US2010/035728 dated Jul. 8, 2010 (3 pages).
International Search Report for PCT/US2010/035783 dated Aug. 23, 2010 (4 pages).
International Search Report for PCT/US2010/047252 dated Nov. 17, 2010 (4 pages).
International Search Report for PCT/US2010/052011 dated Nov. 30, 2010 (3 pages).
International Search Report in International Application No. PCT/US2013/041601, dated Sep. 3, 2013, 3 pages.
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al, "Expedient Synthesis of Potent Cannabinoid Receptor Agonist (−)-CP55,940", Organic Letters, 2005; 7(19); 4181-4183.
Jädersten et al., "Long-term outcome of treatment of anemia in MDS with erythropoietin and G-CSF," Blood, Aug. 2005, 106(3): 803-11.
No Author, Jakavi, Novatis, 2015, 19 pages.
Jakafi, Highlights of Prescribing Information, Incyte Corporation, 2011, revised Mar. 2016, 11 pages.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Japanese Office Action in Japanese Application No. 2015-542764, dated Nov. 6, 2018, 6 pages.
Japanese Office Action in Japanese Application No. 2015-542764, dated Jul. 25, 2017, 5 Pages.
Jee, et al., "Overview: animal models of osteopenia and osteoporosis", J Musculoskel. Neuron, Interact., 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution volume on the values and repeatability of TBUT measurements", Cornea, 2005;24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syndromes", Grafes Arch Clin Exp Ophthalmol, 2004;495-500.
Kaercher, T., "Ocular symptoms and signs in patients with ectodermal dysplasia symdromes", Grafes Arch Clin Exp Ophthalmol, 2004;495-500.
Kamb, "What's wrong with our cancer models?," Nature Reviews, Feb. 2005, 161-165.
Kantarjian et al., "Decitabine improves patient outcomes in myelodysplastic syndromes: results of phase III randomized study," Cancer, Apr. 2006, 106(8): 1794-803.
Kantarjian et al., "Ruxolitinib for Myelofibrosis—An Update of Its Clinical Effects," Clinical Lymphoma, Myeloma & Leukemia, Dec. 2013, 638-645.
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase: Mechanism of Activation and Downstream Effectors.", Cancer Res., 65(6):2047-2053, Mar. 15, 2005.

Killedar et al., "Early pathogenic events associated with Sjogren's syndrome (SjS)-like disease of the NOD mouse using microarray analysis," Lab Invest, Dec. 2006, 86(12): 1243-1260.
Kim, et al., "Zinc-Modified Cyanoborohydride as a Selective Reducing Agent", J. Org. Chem. 50: 1927-1932 (1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents. (Apr. 2010) vol. 20, No. 4, pp. 471-495.
Kojima et al., "A new noninvasive tear stability analysis system for the assessment of dry eyes", Invest Ophthalmol Vis Sci, 2004; May;45(5):1369-74).
Kola, Nature Reviews Drug Discovery 3, pp. 711-715 (2004).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Lett. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-23.
Kuo, et al., "Pd-EDTA as an efficient catalyst for Suzuki-Miyaura reactions in water", Chem Commun 301-3 (2007).
Kuppens et al., "Basal tear turnover and topical timolol in glaucoma patients and healthy controls by Fluorophotometry", Invest Ophthalmol Vis Sci, 1992; 33:3442-3448.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118- 2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol., 147(2):198-205 (2009).
Larock, R., "Comprehensive Organic Transformations", Wiley-VCH, 2nd Ed. (1999) pp. 1949-50, 1958-59, 1976, and 1983-1985.
Larson, "Myelodysplasia: when to treat and how," Best Pract Res Clin Haematol, 2006, 19(2): 293-300.
Leaf, Clifton, Health Administrator vol. XVII, No. 1:172-183 (2005).
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.

(56) References Cited

OTHER PUBLICATIONS

Letter translation of Office Action, Chilean Application No. 3496-2006 as received from the foreign associate (dated Jul. 5, 2010) (4 pages).

Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.

Levitzki, "Tyrosine kineses as targets for cancer therapy", Eur. J. Cancer 38(suppl. 5):S11-S18 (2002).

Levy, et al. "INCB018424 A Selective Janus Kinase 1/2 Inhibitor" Presentation at the 50th American Society of Hematology Annual Meeting (ASH), Dec. 8, 2008.

Levy, et al., INCB18424 Discussion presentation at the American Society of Hematology, 49th Annual Meeting and Exposition, Atlanta, GA. Abstract #558, Dec. 10, 2007 (25 pages).

Li et al., "The synthesis and the antitumor activity of 5,7-disubstituted pyrazolo [1,5-a] pyrimidines," Chinese J Med Chem., Feb. 28, 2007, 17(1):18-22.

Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).

Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.

Lima and Barreiro, "Bioisosterism: a useful strategy for molecular modification and drug design," Curr Med Chem. 2005;12(1):23-49.

Lin, "Constitutive Activation of JAK3/STAT3 in Colon Carcinoma Tumors and Cell Lines", Am J Pathol. 167(4):969-80 (2005).

Lin, et al., "Enantioselective synthesis of Janus kinase inhibitor INCB018424 via an organocatalytic aza-Michael reaction," Organic Letters, (2009), 11(9), 1999-2002.

Ling et al., "Knockdown of STAT3 Expression by RNA Interference Inhibits the Induction of Breast Tumors in Immunocompetent Mice", Cancer Res Apr. 1, 2005 65; 2532.

List et al., "Efficacy of lenalidomide in myelodysplastic syndromes," N Engl J Med, Feb. 2005, 352(6): 549-57.

Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.

Lübbert, et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.

Lübbert, et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.

Lucet et al., "The structural basis of Janus kinas 2 inhibition by a potent and specific pan-Janus kinase inhibitor," Blood, 2006, 107(1):176-183.

Macchi, et al., "Mutations of Jak-3 gene in patients with autosomal severe combined immune deficiency (SCID)", Nature 377:65-8 (1995).

Madden et al, Comparative study of two non-invasive tear film stability techniques. Curr Eye Res, 1994; 13(4):263-9.

Madhusudan et al., "Tyrosine kinase inhibitors in cancer therapy", Clin Biochem., 2004, 37(7):618-35.

Maffioli, et al., "Mild and Reversible Dehydration of Primary Amides with PdCl2 in Aqueous Acetonitrile", Organic Letters vol. 7 No. 23, 5237-39 (2005).

Main et al, "High throughput synthesis of diverse 2,5-disubstituted indoles using titanium carbenoids bearing boronate functionality", Tetrahedron, 64(5):901-914 (2007).

Mainstone et al., "Tear meniscus measurement in the diagnosis of dry eye", Curr Eye Res, 1996; 15:653-661.

Malhotra, "Janus Activated Kinase Inhibition in Myelofibrosis," Indian Journal of Cancer, Sep. 2012, 49(3):260-265.

Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.

Mandal, "Cancer Classification," 2014. Available from: <http://www.news-medical-net/health/Cancer-Classification.aspx, 6 pages.

Manjula, et al., "Rapid Method of Converting Primary Amides to Nitriles and Nitriles to Primary Amides by ZnCl2 using Microwaves under Different Reaction Conditions", Syn. Commun 37:1545-50 (2007).

Manning, et al., "The Protein Kinase Complement of the Human Genome", Science. 2002, 298(5600):1912-16 and 1933-34.

Mao et al., "Advances in research of tyrosine kinases inhibitor of vascular endothelial growth factor receptor," Chinese J New Drugs, Dec. 31, 2008, 17(7):544-550.

March, Jerry, Advanced Organic Chemistry: Reactions, Mechanisms, and Structure, 3rd ed., John Wiley & Sons:New York, pp. 845-855 (1985).

Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.

Maruyama et al., "Effect of environmental conditions on tear dynamics in soft contact lens wearers", Invest Ophthalmol Vis Sci, 2004;45(8):2563-8.

Mascarenhas and Hoffman, "Ruxolitinib: The First FDA Approved Therapy for the Treatment of Myelofibrosis," Clin Cancer Res., Jun. 1, 2012, 18(11):3008-14.

Mathers et al., "Assessment of the tear film with tandem scanning confocal microscopy", Cornea, 1997;16:162-8.

Mathers et al., "Tear film changes associated with normal aging", Cornea, 1996; 15:229-334.

Mathers et al., "Tear flow and evaporation in patients with and without dry eye", Ophthalmology, 1996; 103:664-669.

Mathers et al., "Video imaging of the meibomian gland", Arch Ophthalmol, 1994;112:448-9.

Mathers, "Evaporation from the ocular surface", Exp Eye Res, 2004; 78:389-394.

Maxson et al., "Oncogenic CSF3R Mutations in Chronic Neutrophilic Leukemia and Atypical CML," N. Engl. J. Med., 2013, 368(19):1781-1790.

Mayo Clinic. Available at: < http://www.mayoclinic.com/health/pancreatic-cancer/DS00357 >. 2 pages, retrieved from the Internet Apr. 3, 2013.

Mayo Clinic. Available at: < http://www.mayoclinic.com/health/prostate-cancer-prevention/MC00027 >. 3 pages, retrieved from the Internet Apr. 3, 2013.

Mayo Clinic. Available at: <http://www.mayoclinic.com/health/crohns-disease/DS00104/DSECTION=treatments-and-drugs> 6 pages, retrieved from the Internet May 27, 2013.

Mayo Clinic. Available at: <http://www.mayoclinic.com/health/multiple-sclerosis/DS00188/DSECTION=treatments-and-drugs>. 3 pages, retrieved from the Internet May 27, 2013.

Mayo Clinic. Available at: <http://www.mayoclinic.com/health/myasthenia-gravis/DS00375> 2 pages, retrieved from the Internet May 27, 2013.

Mayo Clinic. Available at: <http://www.mayoclinic.com/health/rheumatoid-arthritis/DS00020/DSECTION=treatments-and-drugs> 3 pages, retrieved from the Internet Jun. 26, 2013.

Mayo Clinic. Available at: <http://www.mayoclinic.org/diseases-conditions/type-1-diabetes/basics/prevention> 2014, 19 pages.

McMillan, "The systemic inflammation-based Glasgow Prognostic Score: a decade of experience in patients with cancer," Cancer Treat Rev, Aug. 2013, 39(5): 534-40.

McNamara et al., "Fluorometry in contact lens research: The next step", Optom Vis Sci, 1998; 75:316-322.

Md Anderson Cancer Center. "Leukemia Prevention and Screening," 2014, 2 pages.

(56) References Cited

OTHER PUBLICATIONS

Md Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986; 64(4):441-4.
Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.
Mesa, R. et al., "Emerging drugs for the therapy of primary and post essential thrombocythemia, post polycythemia vera mylofibrosis", Expert Opinion on Emerging Drugs England, vol. 14, No. 3 (2009) pp. 471-479.
Methods in Molecular Biology: vol. 225, Inflammation Protocols., Winyard, P.G. and Willoughby, D.A., Humana Press, 2003* too voluminous to provide.
Meydan et al., "Inhibition of acute lymphoblastic leukaemia by a Jak-2 inhibitor", Nature. Feb. 15, 1996;379(6566):645-8.
Miethchen, "Micelle-activated reactions. I. Micelle-activated iodination and partial dehalogenation of pyrazoles and 1,2,4-triazoles", Journal P. prakt. Chemie, Band 331, Heft 5, S. 799-805 (1989) (1 page abstract also provided).
Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.
Mishima, et al., "Determination of tear volume and tear flow", Invest Ophthalmol, 1966; 5:264-276.
Mishima, S., "Some physiological aspects of the precorneal tear film", Arch Ophthalmol, 1965;73:233-241.
Mitsunobu, O., "The Use of Diethyl Axodicarboxylate and Triphenylphosphine in Synthesis and Transformation of Natural Products," Synthesis (1): 1-28 (1981).
Miyata, et al., "Stereospecific nucleophilic addition reactions to olefins.", J. Org. Chem. 56:6556-6564 (1991).
Miyaura et al., "Palladium-Catalyzed Cross-Coupling Reactions of Organoboron Compounds," Chem. Rev., 1995, 95, 2457-2483.
Miyoshi et al., "Interleukin-8 concentrations in conjunctival epithelium brush cytology samples correlate with neutrophil, eosinophil infiltration, and corneal damage", Cornea, 2001;20:743-7.
Molldrem, et al., "Antithymocyte globulin for patients with myelodysplastic syndrome," Br J Haematol, Dec. 1997, 99(3): 699-705.
Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan, et al, "JAK mutations in high-risk childhood acute lymphoblastic leukemia", Proc Natl Acad Sci USA. 106:9414-8 (2009).
Mundle, et al. Am J Hematol 1999;60:36-47.
Naka T., "The paradigm of IL-6: from basic science to medicine", Arthritis Res., 2002;4 Suppl 3:S233-42.
Nakagawara, Akira, "Trk receptor tyrosine kinases: A bridge between cancer and neural development." Cancer Letters, 169:107-114, 2001.
Nally et al., "Ocular discomfort and tear film break-up time in dry eye patients: A correlation", Invest Ophthalmol Vis Sci, 2000;41:4:1436 (Poster Presentation).
Naqvi, et al., "A potential role of ruxolitinib in leukemia", Expert Opinion on Investigational Drugs, (Aug. 2011) vol. 20, No. 8, pp. 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
National Institutes of Health, "Study of Ruxolitinib Sustained release formulations in Myelofibrosis Patients," Jul. 23, 2013, Retrieved from the Internet: URL:http://clinicaltrials.gov/ct2/show/results/NCT01340651 [retrieved on Jan. 2, 2014], 4 pages.
Naus, et al., "6-(Het)aryl-7-Deazapurine Ribonucleosides as Novel Potent Cytostatic Agents", J. Med. Chem., 53(1):460-470 (2010).
Neidle, Stephen, Cancer Drug Design and Discovery, (Elsevier/Academic Press, 2008) pp. 427-431.
Nelson et al., "Tear film osmolality determination: an evaluation of potential errors in measurement" Curr Eye Res, Sep.;5(9):677-81, 1986.
Neubauer, H., et al., "Jak2 Deficiency Defines an Essential Developmental Checkpoint in Definitive Hematopoiesis", Cell, 93(3): 397-409 (1998).
Neuner, et al., J. Invest. Dermatol. 1991, 97, 27-33.
Nicholoff et al., "Recent Insights into the immunopathogenesis of psoriasis provide new therapeutic opportunities", J. Clin. Invest., 113; 1664-1675 (2004).
Nichols et al., "The lack of association between signs and symptoms in patients with dry eye disease", Cornea, vol. 23(8):762-770 (2004).
Nichols et al., "The repeatability of clinical measurements of dry eye", Cornea, vol. 23(3):272-85 (2004).
Nishimoto et. al., "Improvement in Castleman's disease by humanized anti-interleukin-6 receptor antibody theraphy," *Blood,* 2000, 95(1):56-61.
Nishio, et al., "Tyrosine kinase-dependent modulation by interferon-α of the ATP-sensitive K+ current in rabbit ventricular myocytes", FEBS Letters, (1999), 445, 87-91.
Nitta, et al., "Peptide-Titanium Complex as Catalyst for Asymmetric Addition of Hydrogen Cyanide to Aldehyde", J. Am. Chem. Soc., 1992, 114, 7969-75 (1992).
Nokhodchi et al., "The role of oral controlled release matrix tablets in drug delivery systems," BioImpacts, 2012, 2(4): 175-187.
Norman, "Selective JAK1 inhibitor and selective Tyk2 inhibitor patents," *Expert Opinion,* Informa Healthcare. 2012, available at: <http://informahealthcare.com/dol/pdfplus/10.1517/13543776.2012.723693>.
Norn, M., "Quantitative tear ferning. Clinical investigations", Acta Ophthalmol (Copenh), Jun. 1994;72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.).
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).

(56) References Cited

OTHER PUBLICATIONS

Office Action in U.S. Appl. No. 14/186,338, dated May 5, 2014, 18 pages.
Office Action received for European Application No. 06 839 328.9 (dated Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (dated Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office, prepared Feb. 5, 2010.
Office Action, European Patent Office Application No. 06 839 328.9 dated Oct. 21, 2010.
Office Action, European Patent Office, dated Nov. 6, 2009.
Office Action, Mexico, Patent Appl. No. MX/a/2008/007635 as received from foreign associate dated Jun. 15, 2010 (1 page).
Office Action, Mexico, Patent Appl. No. MX/a/2008/007635 as received from foreign associate dated Nov. 13, 2009 (4 pages).
Office Action/Examination Report received for Pakistan Application No. 21 1/2009 dated Jan. 18, 2010 (1 page).
Oguz, et al., "The height and radius of the tear meniscus and methods for examining these parameters", Cornea, 2000;19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008, 1 page letter from Foreign Associate enclosing the translation (5 pages) of the Opposition.
Opposition, Ecuador Patent Office, mailed Nov. 8, 2018, Application No. IEPI-2015-25357, 7 pages.
Orlmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/egi/content/abstract/43/12/56?maxtoshow on Aug. 14, 2009.
Palmer, et al., "Multiple roles of ephrins in morphogenesis, neuronal networking, and brain function," Genes & Dev., 17:1429-1450, 2003.
Panteli et al., "Serum interleukin (IL)-1, IL-2, sIL-2Ra, IL-6 and thrombopietin levels in patients with chronic myeloproliferative diseases," British Journal of Haematology, 2003, 130, 709-715.
Pardanani A., "JAK2 inhibitor therapy in myeloproliferative disorders: rationale, preclinical studies and ongoing clinical trialsJAK2 inhibitor therapy in MPD", Leukemia 22, Jan. 23-30, 2008.
Parganas, E., D. Wang, et al., "Jak2 is Essential for Signaling through a Variety of Cytokine Receptors", (1998). Cell, 93(3): 385-95.
Park et al., "Homogeneous Proximity Tyrosine Kinase Assays: Scintillation Proximity Assay versus Homogeneous Time-Resolved Fluorescense", Analytical Biochemistry, 1999, 269, 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani, et al., "Bioisosterism: A Rational Approach in Drug Design", Chem. Rev., 1996, 96, 3147-3176.
Patrick, Graham L., "An Introduction to medicinal chemistry" *Oxford University Press Inc,.* New York, 1995 (31 pages) (cited in Opposition from India dated Nov. 12, 2012.
Pearce et al., "Spatial location studies on the chemical composition of human tear ferns", Ophthalmic Physiol Opt, (2000) vol. 20(4):306-13.
Pearce, et al., "An improved fluorophotometric method for tear turnover assessment", Optom Vis Sci, (2001) 78(1):30-36).
Pedranzini, et al., Cancer Res., 66(19):9714-9721 (2006).
Pensyl et al., "The repeatability of tear mucus ferning grading", Optom Vis Sci, Aug. 1998;75(8):600-4.
Pernis, et al., "JAK-STAT signaling in asthma." J Clin Invest, 109(10): 1279-83 (2002).
Peters, K. G. et al., "Functional Significance of Tie2 Signaling in the Adult Vasculature", 2004, © The Endocrine Society (21 pages).
Pflugfelder, et al., "Evaluation of subjective assessments and objective diagnostic tests for diagnosing tear-film disorders known to cause ocular irritation", Cornea, 1998:17(1):38-56.
Philippine Office Action in Philippine Application No. 1/2015/501089, dated Jan. 14, 2019, 4 pages.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca, Ophthalmology, 2000;107:1841-1849.
Pisella, et al., Conjunctival proinflammatory and proapoptotic effects of Iatanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-8 (with English abstract 20 pages total).
Prchal et al, eds. Williams Hematology, 8th ed., New York: McGraw-Hill; 2010 **Too Voluminous to Provide.
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60, No. 3, 360 Park Avenue South, New York, NY 10010-1710 USA: Mosby-Elsevier, 2009.
Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology: DOI 10.1182/blood-2009-04-214957, 115(15):3109-3117.

(56) References Cited

OTHER PUBLICATIONS

Ravin, L., "Preformulation", Remington's Pharmaceutical Sciences, 17th ed., Mack Publishing Company, Easton, Pa., 1985. Chapter 76, pp. 1409-1423.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk rnyelodysplastic syndromes with karyotypes other than deletion 5q," Blood, Jan. 2008, 111(1): 86-93.
Raza, et al, Int J Hematol 1996a;63:265-278.
Raza, et al., Leuk Res 1996b;20:881-890.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action dated Apr. 20, 2007 filed Jul. 17, 2007 for U.S. Appl. No. 11/313,394 (39 pages).
Response to Action dated Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11,115,702 (8 pages).
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].
Roberts, Jr., et al., JAMA 292(17):2130-2140 (2004).
Robin et al., In vivo transillumination biomicroscopy and photography of meibomian gland dysfunction. Ophthalmology, 1985;92:1423-6.
Rodig, et al., "Disruption of the Jak1 gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.
Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease. Survey of Ophthalmology, Mar. 2001, vol. 45, Supplement 2, S203-S210.
Rolando, M. "Tear mucus ferning test in normal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinas 3 inhibition with CP-690.550 prevents allograft vasculopathy", Transpl Int., 2006 19(12):1014-21.
Rowe et al., Pharmaceutical Excipients, 2009.
Saemann, et al., "Prevention of CD40-triggered dendritic cell maturation and induction of T-cell hyporeactivity by targeting of Janus kinase 3." Am J Transplant, 3(11): 1341-9 (2003).
Saetione et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Santini, et al., PLoS One, 6(8), e23109, pp. 1-8 (2011).
Sawada et al, "Increased Lipophilicity and Subsequent Cell Partitioning Decrease Passive Transcellular Diffusion of Novel, Highly Lipophilic Antioxidents", The Journal of Pharmacology and Experimental Therapeutics, 1999, No. 288, vol. 3, pp. 1317-1326, p. 1321, compound 26.
Schiffer, "Clinical issues in the management of patients with myelodysplasia," Hematology Am Soc Hematol Educ Program, 2006: 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling", Adv Pharmacol. 2000; 47:113-74.
Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).
Search Report in TW Application No. 100117866, dated Dec. 2014, 1 page.
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, et al., "Synthesis of Pyrrolo[2.3-d]pyrimidine 2', 3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica, Acta, 1991, 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003), "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi et al., "The effect of CYP3A4 inhibition or induction on the pharmacokinetics and pharmacodynamics of orally administered ruxolitinib (INCB018424 Phosphate) in Healthy Volunteers," J. Clin. Pharmacol. Jun. 2012;52(6):809-818.
Shi, et al., "The pharmacokinetics, pharmacodynamics, and safety of orally dosed INCB018424 phosphate in heathy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al, "Basic pathogenic mechanisms operating in experimental model acute anterior uveitis," Immunology and Cell Biology, 1998, 76, 497-512.
Smolen, et al, "Effect of interleukin-6 receptor inhibition with tocilizumab in patients with rheumatoid arthritis (Option study): a double-blind, placebo-controlled, randomized trial", Lancet 371:987, 2008 (2008).
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., *Blood*, 2014, 123(24): 3832-3842.
Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.

(56) References Cited

OTHER PUBLICATIONS

Staerk, J., et. al., "JAK1 and Tyk2 activation by the homologous polycythemia vera JAK2 V617F mutation: cross-talk with IGF1 receptor", J Biol Chem., 280:41893-41899 (2005).
State Intellectual Property Office, PR China, Office Action, dated Sep. 3, 2010 Pat. Appl. No. 200680052750.7 (8 pages).
Stirewalt et al., "Predictors of relapse and overall survival in Philadelphia chromosome-positive acute lymphoblastic leukemia after transplantation", Biol Blood Marrow Transplant. Mar. 2003;9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conferenence on the Lacrimal Gland, Tear Film & Ocular Surface and Dry Eye Syndromes, Nov. 20, 2004" (2 pages).
Swerdlow, et al., WHO Classification of Tumours of Haematopoietic and Lymphoid Tissues. 4th Edition. Lyon France: IARC Press; 2008:88-103.
Symington et al., Transplantation, 1992, 54(3): 457-462.
Thailand Office Action in Thailand Application No. 1501002638, dated Jul. 17, 2017 2 pages (English Translation).
Taiwan Search Report in Taiwanese Application No. 102141524, dated May 2, 2017.
Takahashi, et al., "Solvent-Free Reaction Using Pmospwonium Salts: Chlorination of Hydroxyheteroaromatics and dehydration of Primary Amides", Heterocycles 68: 1973-1979 (2006).
Takano et al., "Inflammatory cells in brush cytology samples correlate with the severity of corneal lesions in atopic keratoconjunctivitis", Br J Ophthalmol, 2004;88:1504-5.
Takemoto, et al. (1997). "Proliferation of adult T cell leukemia/ lymphoma cells is associated with the constitutive activation of JAK/STAT proteins." Proc Natl Acad Sci U S A 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tan, et al, "Racemization processes at a quaternary carbon center in the context of the asymmetric Michael reaction", Tetrahedron Lett., 42(30):5021-5023 (2001).
Tang et al., "Knowledge-based design of 7-azaindoles as selective B-Raf inhibitors", Bioorganic & Medicinal Chemistry Letters (2008), 18(16):4610-4614.
Tasian et al., "Understanding the biology of CRLF2-overexpressing acute lymphoblastic leukemia", Critical Reviews in Oncogenesis, (2011) vol. 16, No. 1-2, pp. 13-24.
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis" Mayo Clinic Proceedings, (Dec. 2011) vol. 86, No. 12, pp. 1188-1191.
Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.
Tiffany et al., Meniscometry using the Tearscope-plus (ARVO abstract). Invest Ophthalmol Vis Sci, (2000);42, s37 (1 page).
Tiffany, J., "Refractive index of meibomian and other lipids", Curr Eye Res, (1986);5:887-9.
Ting, et al., "The Synthesis of substituted bipiperidine amide compounds as CCR3 antagonists", Bioorg. Med. Chem. Lett., vol. 15, No. 5, 1 (2005) pp. 1375-1378.
Toyonaga, "Blockade of constitutively activate Janus kinase/signal transducer and activator of transcription-3 pathway inhibits growth of human pancreatic cancer", Cancer Lett. 201(1):107-16 (2003).
Trikha et al., "Targeted anti-interleukin-6 monoclonal antibody therapy for cancer. a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990a ;94:224-30; in Japanese with English abstract.
Tsubota et al., "Conjunctival brush cytology", Acta Cytol, (1990) vol. 34(2):233-5.
Tsubota et al., "Detection by brush cytology of mast cells and eosinophils in allergic and vernal conjunctivitis"; Cornea, (1991) vol. 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).
Ukraine Office Action in Ukraine Application No. a 2015 05798, dated Nov. 20, 2017, 9 pages (English Translation).
Vaillant et al., "Turbidity of pulpy fruit juice: A key factor for predicting cross-flow microfiltration performance," J Membrane Sci., 2008, 325:404-412.
Van Best et al., "Measurement of basal tear turnover using a standardized protocol" Graefe's Arch Clin Exp Ophthalmol, 1995; 233:1-7.
Van Bijsterveld, O., "Diagnostic tests in the sicca syndrome", Arch Ophthalmol, 1969;82:10-14.
Van Rhee et al., "Anti-Interleukin-6 Monoclonal man's Disease," J. Clin. Oncol., 2010, 28(23):3701-3708.
Vanhoutte, Arthritis Rheum 64.10 (2012): S1051-1.
Vannucchi A. et al., "The mTOR Inhibitor, RAD001, Inhibits the Growth of Cells From Patients with Myeloproliferative Neoplasms", Blood: ASH Annual Meeting Absracts, 51$^{st}$ Annual Meeting of the American Society of Hematology, vol. 114, No. 22 (2009) 2 pages.
Vannucchi, A. et al., "Inhibitorsof PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis PPV/PET MF)", Blood, ASH Annual Meeting Abstracts 307, vol. 114, No. 22 (2009) 2 pages.
Vardiman, et al., Blood 2002;100:2292-2302.
Vardiman, et al., Blood 2009;114:937-951.
Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).
Venugopal et al., "Special clinical concerns/problems in the management of MDS and secondary acute myeloid leukemias," Cancer Treat Res, 2001, 108: 257-65.
Verma, et al., "Jak family of kinases in cancer", Cancer and Metastasis Reviews, vol. 22, No. 4, 423-434, DOI: 10.1023/ A:1023805715476 (2003).
Verstovsek et al. "A double-blind, placebo-controlled trial of ruxolitinib for myelofibrosis," N. Eng. J. Med., Mar. 1, 2012:366(9):799-807.
Verstovsek et al., "A Double-Blind, Placebo-Controlled Trial of Ruxolitinib for Myelofibrosis," The New England Journal of Medicine, Mar. 2012, 366(9): 799-807.
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.

(56) References Cited

OTHER PUBLICATIONS

Verstovsek, et al., Blood (ASH Annual Meeting Abstracts) 2010 116: Abstract 313.

Verstovsek, S, et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).

Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).

Verstovsek, S. et al, INCB18424, an Oral, Selective JAK2 Inhibitor, Shows Significant Clinical Activity in a Phase I/II Study in Patient with Primary Myelofibrosis (PMF) and Post Polycythemia Vera/ Essential Thrombocythemia Myelofibrosis (Post-PV/ET MF), presentation at the American Society of Hematology 49th Annual Meeting and Exposition, Dec. 10, 2007 (16 pages).

Verstovsek, Srdan et al., "Characterization of JAK5 V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424, "50th ASH Animal Meeting and Exposition, Abstract No. 2802 (2008).

Vietnamese Office Action in Vietnamese Application No. 12849/SHTT-SC, dated Mar. 8, 2019, 4 pages.

Vitali et al. "The European Community Study Group on diagnostic criteria for Sjogren's syndrome, Sensitivity and specificity of tests for ocular and oral involvement in Sjogren's syndrome." 1994; Ann Rheum Dis, 53(10): 637-47.

Wagh, et al., "Polymers used in ocular dosage form and drug delivery systems", Asian J. Pharm.. pp. 12-17 (Jan. 2008).

WebMD. "Diabetes Health Center." Available at: < http://diabetes.webmd.com/guide/diabetestreatment_care >. 3 pages, retrieved from the Internet May 28, 2013.

Webster's New World Medical Dictionary, Sjogren's syndrome, 2003, Wiley Publishing, printed fro http://www.credoreference.com/entry/webstermed/sjogren_s_syndrome, 2 pages.

Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).

Welch et al., "An approach to a more standardized method of evaluating tear film break-up time", Invest Ophthalmol Vis Sci, 2003; 2485/B324 (abstract only—2 pages).

White et al., "Human basic tear fluid osmolality, I. Importance of sample collection strategy", Acta Ophthalmol (Copenh), Aug. ;71(4):524-9, 1993.

Williams et al., "Carbohydrate Chemistry: Recent Advances", Chem. Rev. 81:589-636 (1981).

Williams, et al, "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.

Wolf, et al., "Burger's Medicinal Chemistry and Drug Discovery", 5th Ed. Part 1, pp. 975-977 (1995).

Wu et al., One-Pot Two-Step Microwave-Assisted Reaction in Construction 4,5-Disubstituted Pyrazolopyrimidines Organic Letters, 2003, 5(20), 3587-3590.

Xiaoyang et al., "Knockdown of STAT3 Expression by RNA Interference Inhibits the Induction of Breast Tumors in Immunocompetent Mice ", Cancer Res Apr. 1, 2005 65; 2532.

Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.

Yamamura et al., "Circulating interleukin-6 levels are elevated in adult T-cell leukaemia/lymphoma patients and correlate with adverse clinical features and survival," Br. J. Haematol., 1998, 100: 129-134.

Yamaoka et al., "Janus kinase (JAK) inhibitors in rheumatoid arthritis", Current Rheumatology Reviews, (Nov. 2011) vol. 7, No. 4, pp. 306-312.

Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.

Yao, et al, "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).

Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).

Ye et al., "The synthesis and the antitumor activity of 5,7-disubstituted pyrazolo [1,5-a]pyrimidines," Chinese J Med Chem., Feb. 28, 2007, 17(1):18-22.

Yokoi et al., "A newly developed video-meibography system featuring a newly designed probe", Jpn J Ophthalmol, 2007; 51: 53-6).

Yokoi et al., "Assessment of meibomian gland function in dry eye using meibometry", Arch Ophthalmol, 1999;117:723-9).

Yokoi et al., "Correlation of tear lipid layer interference patterns with the diagnosis and severity of dry eye", Am J Ophthalmol, 1996;122:818-24.

Yokoi et al., "Non-invasive methods of assessing the tear film", Exp Eye Res, 2004;78:399-407).

Yongjun et al., "Advances in research of tyrosine kinases inhibitor of vascular endothelial growth factor receptor," Chinese J New Drugs, Dec. 31, 2008, 17(7):544-550.

Younes, J. Clin. Oncol., 30(33):1461-1467 (2012).

Yu et al., "Role of Janus Kinase/Signal Transducers and Activators of Transcription in the Pathogenesis of Pancreatitis and Pancreatic Cancer," Gut and Liver, Oct. 2012, 6(4): 417-422.

Yu, et al., "Constitutive activation of the Janus kinase-STAT pathway in T lymphoma overexpressing the Lek protein tyrosine kinase", J Immunol. 159(11):5206-10 (1997).

Zheng, et al., "Discovery of INCBI08201PF-4178903, a potent, selective, and orally bioavailable dual CCR2 and CCR5 antagonist", Bioorganic & Medicinal Chemistry Letters 21 (2011) 1442-45.

Zoppellaro, et al., "A Multifunctional High-Spin Biradical Pyrazolylbipyridine-bisnitronylnitroxide", Org. Lett. 6(26):4929-4932 (2004).

Zou, et al., "Signaling Pathways Activated by Oncogenic Forms of Abl Tyrosine Kinase." Journal of Biological Chemistry, 274(26):18141-18144, 1999.

Opposition (Actavis), European Patent Office, EP Patent No. EP2173752, mailed Jan. 20, 2015, 20 pages.

Opposition (Generics), European Patent Office, EP2173752, mailed Jan. 20, 2015, 18 pages.

U.S. National Institute of Health, "Study of Ruxolitinib," Dec. 3, 2008, available at www.clinicaltrials.gov, 11 pages.

Harper Collins Publishers, Collins English Dictionary, "in vitro" and "in vivo", p. 852, 2007.

Research Gate, "What is the difference between Ex vivo and In vitro?", Dec. 18, 2014, available at http://www.researchgate.net/post/What_is_the_difference_between_Ex_vivo_and_in_vitro, 6 pages.

Gadamasetti et al., "Process Chemistry in the Pharmaceutical Industry," Challenges in an Ever Changing Climate, 2008, vol. 2, pp. 49-63.

U.S. National Institute of Health, "Open Label Ruxolitinib (INCB018424) in Patients with Myelofibrosis and Post Polycythemia Vera/Essential Thrombocythemia Myelofibrosis," Dec. 19, 2014, available at www.clinicaltrials.gov, 4 pages.

Office Action, Intellectual Property Office of Singapore, Application No. 2012043428, dated Sep. 26, 2014 (25 pages).

(56) References Cited

OTHER PUBLICATIONS

U.S. National Institute of Health, "Ruxolitinib for Chronic Myeloid Leukemia (CML) With Minimal Residual Disease (MRD)," Dec. 14, 2012, available at www.clinicaltrials.gov, 4 pages.
U.S. National Institute of Health, "Study of Ruxolitinib Plus Decitabine in Patients With Acute Myeloid Leukemia (AML)," dated Sep. 26, 2014, available at www.clinicaltrials.gov, 4 pages.
U.S. National Institute of Health, "Ruxolitinib for Pracinostat Combination Therapy for Patients With Mylofibrosis (MF)," dated Oct. 10, 2014, available at www.clinicaltrials.gov, 4 pages.
U.S. National Institute of Health, "Ruxolitinib or Dasatinib With Chemotherapy in Patients With Philadelphia Chromosome (Ph)-Like Acute Lymphoblastic Leukemia (ALL)," dated Apr. 15, 2015, available at www.clinicaltrials.gov, 8 pages.
U.S. National Institute of Health, "Ruxolitinib Prior to Transplant in Patients With Myelofibrosis," dated Feb. 8, 2013, available at www.clinicaltrials.gov, 6 pages.
U.S. National Institute of Health, "Ruxolitinib for Patients With Low or Intermediate-1 Risk Myelodysplastic Syndrome (MDS)," dated Jul. 5, 2013, available at www.clinicaltrials.gov, 3 pages.
U.S. National Institute of Health, "Study of Ruxolitinib in Colorectal Cancer Patients," dated Apr. 17, 2014, available at www.clinicaltrials.gov, 4 pages.
U.S. National Institute of Health, "Ruxolitinib in Combination With Autotransplant," dated May 28, 2015, available at www.clinicaltrials.gov, 4 pages.
U.S. National Institute of Health, "Phase I/II Study of Ruxolitinib for Acute Leukemia," dated Nov. 30, 2010, available at www.clinicaltrials.gov, 3 pages.
U.S. National Institute of Health, "Administration of Jakafi (Ruxolitinib) for Symptom Control of Patients With Chronic Lymphocytic Leukemia (CLL): Phase II," dated May 2, 2014, available at www.clinicaltrials.gov, 4 pages.
U.S. National Institute of Health, "TGR-1202+Ruxolitinib PMF PPV-MF PET-MF MDS/MPN Polycythemia Vera Resistant to Hydroxyurea," dated Jul. 1, 2015, available at www.clinicaltrials.gov, 4 pages.
U.S. National Institute of Health, "Alternative Dosing Strategy of Ruxolitinib in Patients With Myelofibrosis," dated Sep. 23, 2011, available at www.clinicaltrials.gov, 6 pages.
U.S. National Institute of Health, "Ruxolitinib and Lenalidomide for Patients With Myelofibrosis," dated Jun. 14, 2011, available at www.clinicaltrials.gov, 4 pages.
U.S. National Institute of Health, "Study of Ruxolitinib (INCB018424) Sustained Release Formulation in Myelofibrosis Patients," dated Apr. 21, 2011, available at www.clinicaltrials.gov, 4 pages.
U.S. National Institute of Health, "Raxolitinib Efficacy and Safety in Patients With HU Resistant or Intolerant Polycythemia Vera vs Best Available Therapy. (Response 2)," dated Jan. 14, 2014, available at www.clinicaltrials.gov, 4 pages.
U.S. National Insitute of Health, "Phase III Study Investigating the Efficacy and Safety of Ruxolitnib in Early Myelofibrosis Patients With High Molecular Risk Mutations," dated Oct. 27, 2015, available at www.clinicaltrials.gov, 4 pages.
U.S. National Institute of Health, "Ruxolitinib in Combination With Pemetrexed/Cisplatin in Non Small Cell Lung Cancer," dated Apr. 17, 2014, available at www.clinicaltrials.gov, 4 pages.
U.S. National Institute of Health, "Ruxolitinib in Combination With Trastuzumab in Metastatic HER2 Positive Breast Cancer," dated Feb. 18, 2014, available at www.clinicaltrials.gov, 5 pages.
U.S. National Institute of Health, "Ruxolitinib W/ Preop Chemo for Triple Negative Inflammatory Brca," dated Jan. 11, 2014, available at www.clinicaltrials.gov, 4 pages.
U.S. National Institute of Health, "Trial of Ruxolitinib and Erlotinib in Patients With EGFR-mutant Lung Adenocarcinoma With Acquired Resistance to Erlotinib," dated Jun. 2, 2014, available at www.clinicaltrials.gov, 4 pages.
U.S. National Institute of Health, "Study to Determine the Safety and Efficacy of Ruxolitinib (INCB018424) in Patients With Polycythemia Vera or Essential Thrombocythemia," dated Jul. 29, 2008, available at www.clinicaltrials.gov, 5 pages.
U.S. National Institute of Health, "Panobinostat and Ruxolitinib in Myelofibrosis (PRIME Trial) (PRIME)," dated Sep. 14, 2012, available at www.clinicaltrials.gov, 4 pages.
U.S. National Institute of Health, "Pharmacodynamic Effects and Predictive Biomarkers With Ruxolitinib in Operable Head and Neck Cancer," dated Oct. 14, 2015, available at www.clinicaltrials.gov, 4 pages.
U.S. National Institute of Health, "Pilot Study to Evaluate of Ruxolitinib in Alopecia Areata," dated Sep. 23, 2013, available at www.clinicaltrials.gov, 4 pages.
U.S. National Institute of Health, "Ruxolitinib Phosphate, Tacrolimus and Sirolimus in Preventing Acute Graft-versus-Host Disease During Reduced Intensity Donor Hematopoietic Cell Transplant in Patients With Myelofibrosis," dated Aug. 18, 2015, available at www.clinicaltrials.gov, 6 pages.
U.S. National Institute of Health, "Ruxolitinib in Combination With Nilotinib in Chronic Myeloid Leukemia (CML) Patients," dated Oct. 3, 2012, available at www.clinicaltrials.gov, 4 pages.
U.S. National Institute of Health, "A Phase II Study of Re-treatment of Myelofibrosis Patients With Ruxolitinib/Jakavi After Treatment Interruption Due to Loss of Response and/or Adverse Event (Re Treatment Trial)," dated Mar. 6, 2014, available at www.clinicaltrials.gov, 3 pages.
U.S. National Institute of Health, "A Sequential Two-Stage Dose Escalation Study to Evaluate the Safety and Efficacy of Ruxolitinib," dated Jan. 24, 2013, available at www.clinicaltrials.gov, 5 pages.
U.S. National Institute of Health, "Dose Escalation Study to Determine the Maximum Tolerated Dose of the Combination of Ruxolitinib and Bortezomib in Patients with Relapsed or Refractory Lymphoma," dated Nov. 20, 2015, available at www.clinicaltrials.gov, 4 pages.
U.S. National Institute of Health, "Study of Ruxolitinib (INCB018424) Administered Orally to Patients With Androgen Independent Metastatic Prostate Cancer," dated Mar. 12, 2008, available at www.clinicaltrials.gov, 4 pages.
U.S. National Institute of Health, "Ruxolitinib Phosphate in Treating Patients With Chronic Neutrophilic Leukemia or Atypical Chronic Myeloid Leukemia," dated Mar. 18, 2014, available at www.clinicaltrials.gov, 5 pages.
U.S. National Institute of Health, "Panobinostat and Ruxolitinib in Primary Myelofibrosis, Post-polycythemia Vera-myelofibrosis or Post-essential Thrombocythemia-myelofibrosis," dated Jun. 27, 2011, available at www.clinicaltrials.gov, 4 pages.
U.S. National Institute of Health, "Momelotinib Versus Ruxolitinib in Subjects With Myelofibrosis (Simplify 1)," dated Oct. 22, 2013, available at www.clinicaltrials.gov, 4 pages.
U.S. National Institute of Health, "A Study to Determine the Effect and Safety of an Oral Janus Kinase 2 (JAK2)-Inhibitor (Ruxolitinib; INBC018424) in Patients With Multiple Myeloma," dated Mar. 12, 2008, available at www.clinicaltrials.gov, 3 pages.
U.S. National Institute of Health, "Ruxolitinib Phosphate and Danazol in Treating Anemia in Patients With Myelofibrosis," dated Nov. 19, 2012, available at www.clinicaltrials.gov, 5 pages.
U.S. National Institute of Health, "Safety and Tolerability of Combined Treatment With Nilotinib and Ruxolitinib in CML and Ph+ALL Patients (CoRNea)," dated Sep. 17, 2014, available at www.clinicaltrials.gov, 4 pages.
U.S. National Institute of Health, "Controlled Myelofibrosis Study with Oral JAK Inhibitor Treatment: The COMFORT-1 Trial," dated Aug. 4, 2009, available at www.clinicaltrials.gov, 5 pages.
U.S. National Institute of Health, "Study of Ruxolitinib in Pancreatic Cancer Patients (RECAP)," dated Aug. 22, 2011, available at www.clinicaltrials.gov, 3 pages.
U.S. National Institute of Health, "A Study of Ruxolitinib in Combination With Capecitabine in Subjects With Advanced or Metastatic HER2-negative Breast Cancer," dated Apr. 18, 2014, available at www.clinicaltrials.gov, 3 pages.
U.S. National Institute of Health, "Open Label Ruxolitinib (INCB018424) in Patients With Myelofibrosis and Post Polycythemia Vera/Essential Thombrocythemia Myelofibrosis," dated Jul. 30, 2007, available at www.clinicaltrials.gov, 4 pages.

(56) References Cited

OTHER PUBLICATIONS

U.S. National Institute of Health, "Study of Combination Ruxolitinib and Decitabine Treatment for Accelerated Phase MPN or Post-MPN AML," dated Feb. 27, 2014, available at www.clinicaltrials.gov, 4 pages.
U.S. National Institute of Health, "Ruxolitinib in GvHD (RIG)," dated Mar. 10, 2015, available at www.clinicaltrials.gov, 4 pages.
U.S. National Institute of Health, "A Pilot Study of Ruxolitinib in Secondary Hemophagocytic Syndrome," dated Jan. 22, 2015, available at www.clinicaltrials.gov, 3 pages.
U.S. National Institute of Health, "Adding Ruxolitinib to a Combination of Dasatinib Plus Dexamethasone in Remission Induction Therapy in Newly Diagnosed Philadelphia Chromosome-Positive Acute Lymphoblastic Leukemia Patients Aged 40 Years or Older," dated Jul. 8, 2015, available at www.clinicaltrials.gov, 4 pages.
U.S. National Institute of Health, "Ruxolitinib Phosphate (Oral JAK Inhibitor INCB18424) in Treating Patients With Relapsed or Refractory Diffuse Large B-Cell or Peripheral T-Cell Non-Hodgkin Lymphoma," dated Sep. 5, 2011, available at www.clinicaltrials.gov, 4 pages.
U.S. National Institute of Health, "Ruxolitinib (INCB018424) in Subjects With Primary Myelofibrosis, Post Essential Thrombocythemia-myelofibrosis and Post Polycythemia Vera-myelofibrosis," dated May 4, 2011, available at www.clinicaltrials.gov, 3 pages.
U.S. National Institute of Health, "Expanded Treatment Protocol (ETP) of Ruxolitinib in Patients With Polycythemia Vera Who Are Hydroxyurea Resistant or Intolerant and for Whom no Treatment Alternatives Are Available," dated Nov. 5, 2014, available at www.clinicaltrials.gov, 3 pages.
U.S. National Insitute of Health, "Ruxolitinib and Pomalidomide Combination Therapy in Patients With Primary and Secondary MF (POMINC)," dated Jul. 16, 2012, available at www.clinicaltrials.gov, 4 pages.
U.S. National Institute of Health, "Study of Ruxolitinib in Pancreatic Cancer Patients (Janus 1)," dated Apr. 16, 2014, available at www.clinicaltrials.gov, 3 pages.
U.S. National Institute of Health, "A Study of Ruxolitinib in Pancreatic Cancer Patients," dated Apr. 17, 2014, available at www.clinicaltrials.gov, 3 pages.
U.S. National Institute of Health, "Randomized Switch Study From Hydroxyurea to Ruxolitinib for Relief of Polycythemia Vera Symptoms: The Relief Study," dated Jun. 29, 2012, available at www.clinicaltrials.gov, 3 pages.
U.S. National Institute of Health, "A Study of INCB018424 Phosphate Cream When Applied to Patients With Plaque Psoriasis," dated Jan. 8, 2009, available at www.clinicaltrials.gov, 3 pages.
U.S. National Institute of Health, "Ruxolitinib in Patients With Breast Cancer," dated Mar. 20, 2012, available at www.clinicaltrials.gov, 3 pages.
U.S. National Insitute of Health, "Phase I/II Study of Nilotinib/Ruxolitinib Therapy for TKI Resistant Ph-Leukemia," dated Jul. 28, 2013, available at www.clinicaltrials.gov, 5 pages.
U.S. National Institute of Health, "Safety, Tolerability, and Pharmacokinetics of Idelalisib in Adults Receiving Ruxolitinib as Therapy for Primary, Post-Polycythemia Vera, or Post-Essential Thrombocythemia Myelofibrosis With Progressive or Relapsed Disease," dated May 1, 2015, available at www.clinicaltrials.gov, 4 pages.
U.S. National Institute of Health, "Study of the JAK Inhibitor Ruxolitinib Administered Orally to Patients With Primary Myelofibrosis (PMF), Post-Polycythemia Vera-Myelofibrosis (PPV-MF) or Post-Essential Thrombocythemia-Myelofibrosis (PET-MF)," dated Mar. 14, 2011, available at www.clinicaltrials.gov, 4 pages.
U.S. National Institute of Health, "Ruxolitinib for Adult T-Cell Leukemia," dated Oct. 20, 2012, available at www.clinicaltrials.gov, 4 pages.
U.S. National Institute of Health, "An Opel-Label Study of Ruxolitinib Given With Chemotherapy in Patients With Advanced Solid Tumors," dated Mar. 28, 2013, available at www.clinicaltrials.gov, 3 pages.

U.S. National Institute of Health, "Ruxolitinib in the Treatment of Chronic Lymphocytic Leukemia," dated Dec. 3, 2013, available at www.clinicaltrials.gov, 4 pages.
U.S. National Institute of Health, "Evaluating the Safety and Tolerability of Ruxolitinib Antiretroviral-Treated HIV-Infected Adults," dated Jun. 16, 2015, availabe at www.clinicaltrials.gov, 6 pages.
U.S,. National Institute of Health, "Evaluation of RUX and AZA Combination as a Therapy for Patients With Myelofibrosis and Myelodysplastic Syndrome/ Myeloproliferative Neoplasm," dated Feb. 6, 2013, available at www.clinicaltrials.gov, 5 pages.
U.S. National Institute of Health, "Study of the Safety of PIM447 in Combination With Ruxolitinib (INC424) and LEE011 in Patients With Myelofibrosis," dated Feb. 6, 2015, available at www.clinicaltrials.gov, 5 pages.
U.S. National Institute of Health, "Ruxolitinib for Chuvash Polycythemia," dated Nov. 7, 2012, available at www.clinicaltrials.gov, 2 pages.
U.S. National Institute of Health, "A Study to Evaluate Efficacy and Safety of Vismodegib (Erivedge) in Combination With Ruxolitinib for the Treatment of Intermediate- or High-Risk Myelofibrosis (MF)," dated Oct. 29, 2015, available at www.clinicaltrials.gov, 3 pages.
U.S. National Institute of Health, "Ruxolitinib in Estrogen Receptor Positive Breast Cancer," dated May 7, 2012, available at www.clinicaltrials.gov, 3 pages.
U.S. National Institute of Health, "Pilot Study of Ruxolitinib in Relapsed or Refractory Hodgkin Lymphoma and Primary Mediastinal Large B-cell Lymphoma (JAK2)," dated Oct. 9, 2013, available at www.clinicaltrials.gov, 4 pages.
U.S. National Institute of Health, "Study of Ruxolitinib in the Treatment of Cachexia in Patients With Tumor-Associated Chronic Wasting Diseases," dated Feb. 21, 2014, available at www.clinicaltrials.gov, 4 pages.
U.S. National Institute of Health, "INCB018424 in Patients With Advanced Hematologic Malignancies," dated May 5, 2008, available at www.clinicaltrials.gov, 4 pages.
U.S. National Institute of Health, "A Clinical Study of Ruxolitinib in Patients With Primary Myelofibrosis (PM), Post-polycythemia Vera (PV) Myelofibrosis or Post-essential Thrombocythemia (ET) Myelofibrosis," dated Mar. 12, 2014, available at www.clinicaltrials.gov, 4 pages.
U.S. National Institute of Health, "A Dose Ranging Study of the Effect of INCB018424 Phosphate Cream When Applied to Patients With Plaque Psoriasis," dated Oct. 21, 2008, available at www.clinicaltrials.gov, 3 pages.
U.S. National Institute of Health, "Phase I Study of the Combination of Afatinib and Ruxolitinib in Patients With Treatment-refractory Non-Small Cell Lung Cancer (NSCLC)," dated Apr. 23, 2014, available at www.clinicaltrials.gov, 3 pages.
U.S. National Institute of Health, "INCB18424 in Treating Young Patients With Relapsed or Refractory Solid Tumor, Leukemia, or Myeloproliferative Disease," dated Jul. 15, 2010, available at www.clinicaltrials.gov, 5 pages.
U.S. National Institute of Health, "The Ruxo-BEAT Trial in Patients With High-risk Polycythemia Vera or High-risk Essential Thrombocythemia (Ruxo-BEAT)," dated Oct. 1, 2015, available at www.clinicaltrials.gov, 5 pages.
U.S. National Institute of Health, "A Study With INCB018424 Phosphate Cream Applied Topically to Subjects With Alopecia Areata (AA)," dated Sep. 16, 2015, available at www.clinicaltrials.gov, 3 pages.
U.S. National Institute of Health, "Efficacy and Safety of Simtuzumab in Adults With Primary, Post Polycythemia Vera or Post Essential Thrombocythemia Myelofibrosis," dated Jun. 6, 2011, available at www.clinicaltrials.gov, 4 pages.
U.S. National Institute of Health, "Study of Efficacy and Safety in Polycythemia Vera Subjects Who Are Resistant to or Intolerant of Hydroxyurea: JAK Inhibitor INC424 (INCB018424) Tablets Versus Best Available Care: (The RESPONSE Trial)," dated Nov. 17, 2010, available at www.clinicaltrials.gov, 4 pages.
U.S. National Institute of Health, "A Study Exploring the Safety, Tolerability and Efficacy of a 4 Week Course of INCB018424 in

(56) References Cited

OTHER PUBLICATIONS

Subjects With Active Rheumatoid Arthritis," dated Oct. 24, 2007, available at www.clinicaltrials.gov, 4 pages.
U.S. National Institute of Health, "JAK2 Inhibitors Ruxolitinib in Patients With Myelofibrosis," dated Dec. 21, 2012, available at www.clinicaltrials.gov, 4 pages.
U.S. National Institute of Health, "Single-Agent Glasdegib in Patients With Myelofibrosis Previously Treated With Ruxolitinib," dated Aug. 25, 2014, available at www.clinicaltrials.gov, 4 pages.
U.S. National Institute of Health, "CINC424A2X01B Rollover Protocol," dated Mar. 6, 2015, available at www.clinicaltrials.gov, 4 pages.
U.S. National Institute of Health, "JAK-inhibition in Recurrent Classical Hodgkin Lymphoma (JeRiCHO)," dated Jun. 12, 2014, available at www.clinicaltrials.gov, 3 pages.
U.S. National Institute of Health, "Open Label, Safety and Efficacy Study of Topical Investigational Drug to Treat Patients With Psoriasis," dated Jan. 21, 2008, available at www.clinicaltrials.gov, 3 pages.
U.S. National Institute of Health, "Asian Phase II Study of INC424 in Patients With Primary Myelofibrosis (MF), Post-PV MF or Post-ET MF," dated Jul. 11, 2011, available at www.clinicaltrials.gov, 4 pages.
U.S. National Institute of Health, "A Phase II Study of Oral JAK1/JAK2 Inhibitor INC424 in Adult Patients With Relapsed/Refractory Classical Hodgkin's Lymphoma (HIJAK)," dated Jun. 11, 2013, available atwww.clinicaltrials.gov, 4 pages.
U.S. National Institute of Health, "Phase II, Open Label, Single Arm Study of SAR302503 in Myelofibrosis Patients Previously Treated With Ruxolitinib (JAKARTA2)," dated Jan. 27, 2012, available at www.clinicaltrials.gov, 4 pages.
U.S. National Institute of Health, "Controlled Myelofibrosis Study With Oral Janus-associated Kinase (JAK) Inhibitor Treatment-II: The COMFORT-II Trial," dated Jul. 6, 2009, available at www.clinicaltrials.gov, 4 pages.
U.S. National Institute of Health, "Study of Effficacy and Safety of INC424 in Regularly Transfused Patients With Thalassemia," dated Jan. 28, 2014, available at www.clinicaltrials.gov, 3 pages.
U.S. National Institute of Health, "Genomics-Based Target Therapy for Children With Relapsed or Refractory Malignancy," dated Nov. 29, 2015, available at www.clinicaltrials.gov, 3 pages.
U.S. National Institute of Health, "Efficacy of Momelotinib Versus Best Available Therapy in Anemic or Thrembocytopenic Subjects With Primary Myelofibrosis (MF), Post-Polycythemia Vera MF, or Post-essential Thrornbocythemia MF (Simplify 2)," dated Mar. 28, 2014, available at www.clinicaltrials.gov, 4 pages.
U.S. National Institute of Health, "Exploratory Phase II Study of INC424 Patients With Primary Myelofibrosis (PMF) or Post Polycythaemia Myelofibrosis (PPV MF) or Post Essential Thrombocythaemia Myelofibrosis (PET-MF) (MACS2030)," dated Mar. 16, 2012, available at www.clinicaltrials.gov, 4 pages.
U.S. National Institute of Health, "INC424 for Patients With Myelofibrosis, Post Polycythemia Myelofibrosis or Post-essential Thrombocythemia Myelofibrosis (JUMP)," dated Dec. 13, 2011, available at www.clinicaltrials.gov, 3 pages.
U.S. National Institute of Health, "N-of-1 Trial: Actionable Target Identification in Metastatic Cancer for Palliative Systemic Therapy (MetAction)," dated Apr. 13, 2014, available at www.clinicaltrials.gov, 4 pages.
U.S. National Institute of Health, "A Phase Ib/II Dose-finding Study to Assess the Safety and Efficacy of LDE225+INC424 in Patients With MF," dated Feb. 6, 2013, available at www.clinicaltrials.gov, 5 pages.
U.S. National Institute of Health, "A Study of LY2784544 in Participants With Myeloproliferative Neoplasms," dated May 1, 2012, available at www.clinicaltrials.gov, 3 pages.
U.S. National Institute of Health, "The Role of JAK2 in Alveolar Macrophages (AM's) in Chronic Beryllium Disease (CBD)," dated Oct. 29, 2015, available at www.clinicaltrials.gov, 4 pages.
U.S. National Institute of Health, "High Throughput Drug Sensitivity Assay and Genomes—Guided Treatment of Patients With Relapsed or Refractory Acute Leukemia," dated Aug. 25, 2015, available at www.clinicaltrials.gov, 4 pages.
U.S. National Institute of Health, "Oral Pacritinib Versus Best Available Therapy to Treat Myelofibrosis With Thrombocytopenia (PAC326)," dated Feb. 3, 2014, available at www.clinicaltrials.gov, 3 pages.
Submission in Opposition Proceedings in European Application No. 08770794.9, Actavis Group PTC ehf, dated Mar. 19, 2014, 7 pages.
Submission in Opposition Proceedings in European Application No. 08770794.9, Incyte Corporation, dated Jun. 5, 2015, 14 pages.
Summons to Attend Oral Proceedings in European Application No. 08770794.9, dated Nov. 30, 2015, 18 pages.
Summons to Attend Oral Proceedings in European Application No. 08770794.9, dated Jan. 29, 2016, 18 pages.
New Zealand Office Action in New Zealand Application No. 748448, dated Apr. 3, 2019, 5 pages.
Brown et al., "Compartmental Absorption Modeling and Site of Absorption Studies to Determine Feasibility of an Extended-Release Formulation of an HIV-1 Attachment Inhibitor Phosphate Ester Prodrug," J Pharm. Sci., Jun. 2013, 102(6):1742-1751.
Jia et al., "Pharmacokinetics of Single-Dose and Multi-Dose of Lovastatin/Niacin ER Tablet in Healthy Volunteers," Chromatography Research International, 2012, 11 pages.
Tahara et al., "Overall mechanism behind matrix sustained release (SR) tablets prepared with hydroxypropyl methylcellulose 2910," Journal of Controlled Release, Jul. 1995, 35(1):59-66.
Tanaka et al., "Modified- versus immediate-release tofacitinib in Japanese rheumatoid arthritis patients: a randomized, phase III, non-inferiority study," Rheumatology, 2019, 58:70-79.
Canadian Office Action in Canadian Application No. 2,890,755, dated Aug. 21, 2020, 5 pages.
Chinese Office Action in Chinese Application No. 201380070296.8, dated May 9, 2020, 9 pages.
Costa Rican Office Action in Costa Rican Application No. 2015-0265, dated Jun. 17, 2020, 34 pages.
European Summons to Attend Oral Proceedings in European Application No. 13798840.8, dated Apr. 1, 2020, 6 pages.
Israeli Office Action in Israeli Application No. 238,765, dated Sep. 17, 2020, 12 pages.
Korean Office Action in Korean Application No. 10-2015-7015681, dated Apr. 22, 2020, 19 pages.
Mexican Office Action in Mexican Application No. MX/a/2015/005947, dated Aug. 2020, 5 pages.
Peruvian Office Action in Peruvian Application No. 624-2015, dated Nov. 26, 2019, 15 pages.
Philippine Office Action in Philippine Application No. 1/2015/501089, dated Jun. 23, 2020, 4 pages.

\* cited by examiner

SUSTAINED-RELEASE DOSAGE FORMS OF RUXOLITINIB

FIELD OF THE INVENTION

The present invention relates to sustained-release formulations and dosage forms of ruxolitinib, or a pharmaceutically acceptable salt thereof, which are useful in the treatment of Janus kinase-associated diseases such as myeloproliferative disorders.

BACKGROUND OF THE INVENTION

Ruxolitinib ((3R)-3-cyclopentyl-3-[4-(7H-pyrrolo[2,3-d]pyrimidin-4-yl)pyrazol-1-yl]propanenitrile) is the first FDA approved Janus kinase (JAK) inhibitor and is the only drug currently approved for treatment of myelofibrosis. Mascarenhas, J. et al. Clin Cancer Res. 2012 Jun. 1; 18(11):3008-14. Epub 2012 Apr. 2. The compound has been shown in the clinic to effectively reduce spleen volume and improve total symptom scores in patients suffering from myelofibrosis. See, e.g., Verstovsek, S., et al. "A double-blind, placebo-controlled trial of ruxolitinib for myelofibrosis," N. Eng. J. Med., 2012, Mar. 1:366(9):799-807, which is incorporated herein by reference in its entirety, which reports the results of a Phase 3 clinical trial (COMFORT-I Study) of ruxolitinib for myelofibrosis. See also, Harrison, C. et al., "JAK inhibition with ruxolitinib versus best available therapy for myelofibrosis," N. Eng. J. Med., 2012, Mar. 1; 366(9):787-98 reporting Phase 3 clinical trial results of the COMFORT-II study, which is incorporated herein by reference in its entirety.

To date, all published human clinical data for ruxolitinib relate to dosing of an immediate-release formulation. However, ruxolitinib is a BCS Class I molecule with rapid oral absorption and a short half-life of about 3 hours. See, Shi et al., J. Clin. Pharmacol. 2012 June; 52(6):809-18. Epub 2011 May 20. These properties result in a high peak/trough plasma concentration ratio in human subjects leading to multiple daily doses for optimal treatment, and potentially contributing to problems with patient compliance and unwanted side effects.

Ruxolitinib therapy is often associated with the adverse events of thrombocytopenia (low platelet count) and anemia (low hemoglobin). Thrombocytopenia is dose-dependent and considered the dose-limiting toxic effect.

Accordingly, there is a need for new and improved formulations of ruxolitinib that not only mitigate adverse side-effects in patients, but still achieve therapeutic efficacy, and also facilitate administration of the drug such as by reducing the number of doses required to achieve a therapeutic effect. The sustained-release formulations provided herein help meet these and other needs.

SUMMARY OF THE INVENTION

The present invention is directed to a sustained-release dosage form comprising at least one active ingredient which is ruxolitinib, or a pharmaceutically acceptable salt thereof, wherein the ruxolitinib, or pharmaceutically acceptable salt thereof, is present in the dosage form in an amount of about 10 to about 60 mg on a free base basis.

The present invention is further directed to a method of treating a disease associated with JAK activity in a patient in need thereof, comprising administering the sustained-release dosage form of the invention to said patient.

DETAILED DESCRIPTION

Sustained-Release Dosage Forms

Figure 1:
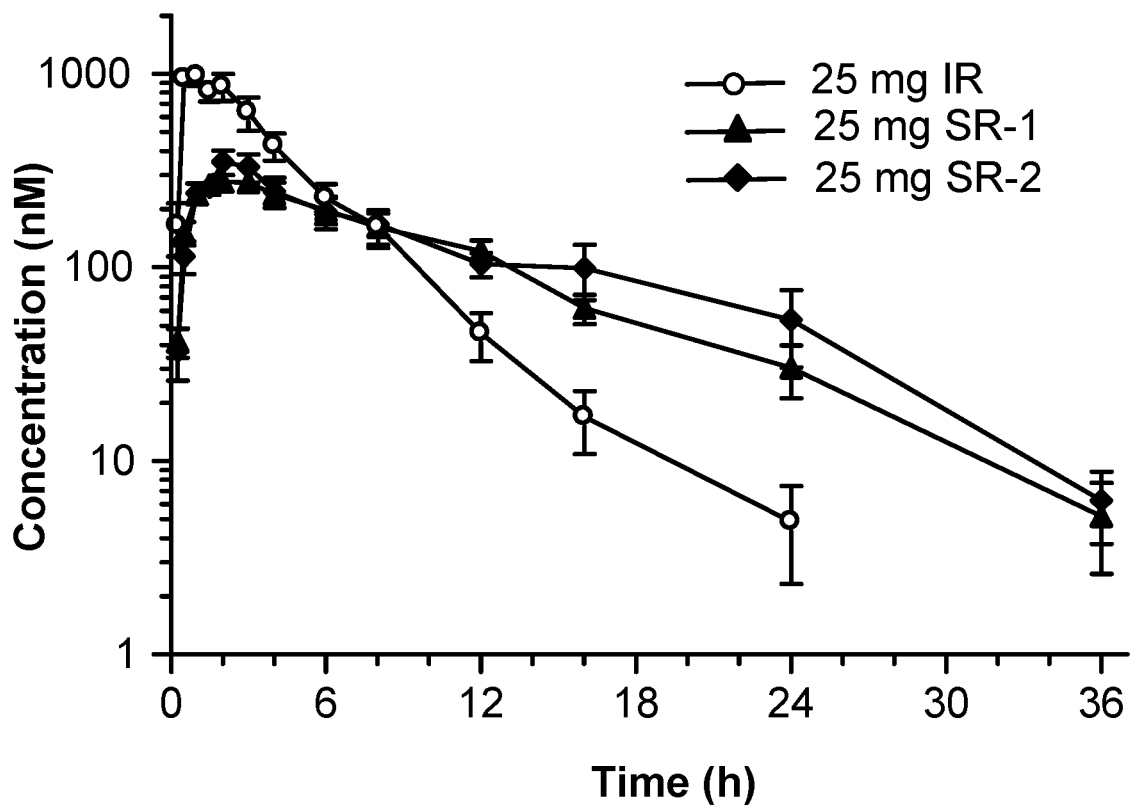
FIG. 1 shows a graph comparing plasma concentrations of ruxolitinib after administration of a single dose of either 25 mg immediate-release or 25 mg sustained-release formulation in fasted, healthy human subjects.

The present invention provides, inter alia, an oral, sustained-release dosage form comprising ruxolitinib, or a pharmaceutically acceptable salt thereof, as an active ingredient. The dosage form can contain ruxolitinib, or a pharmaceutically acceptable salt thereof, in an amount of about 10 to about 60 mg, about 10 to about 40 mg, about 20 to about 40 mg, or about 20 to about 30 mg on a free base basis. In some embodiments, the dosage form contains about 10 mg, about 12.5 mg, about 20 mg, about 25 mg, about 30 mg, about 37.5 mg, about 40 mg, about 50 mg, or about 60 mg on a free base basis. In some embodiments, the dosage form contains about 25 mg of ruxolitinib on a free base basis. The phrase "on a free base basis" indicates that the amount of ruxolitinib or salt thereof in the dosage form is measured based on the molecular weight of ruxolitinib free base only, even when the actual active ingredient is a salt of ruxolitinib having a different molecular weight than the free base. For example, the conversion factor for ruxolitinib phosphate salt to free base is 0.7575.

The structure, preparation, and characterization of ruxolitinib, and pharmaceutically acceptable salts thereof, are described in, e.g., U.S. Pat. No. 7,598,257 and US Pat. Pub. No. 2008/0312259, each of which is incorporated herein by reference in its entirety. In some embodiments, the active ingredient is a pharmaceutically acceptable salt of ruxolitinib, such as the maleic acid salt, sulfuric acid salt, or phosphoric acid salt. In some embodiments, the active ingredient is ruxolitinib phosphate (i.e., phosphoric acid salt of ruxolitinib).

The dosage form of the invention comprises a sustained-release formulation of ruxolitinib, or a pharmaceutically acceptable salt thereof. As used herein, "sustained-release" is used as generally understood in the art and refers to a formulation designed to slowly release the active ingredient into a patient after oral administration and to maintain an essentially steady, therapeutically effective plasma level of active ingredient over a relatively long period of time, such as about 8 to about 24 hours or longer.

The dosage forms of the invention include a sustained-release matrix former. Example sustained-release matrix formers include cellulosic ethers such as hydroxypropyl methylcellulose (HPMC, hypromellose) which is a high viscosity polymer. The sustained-release dosage forms of the invention can include, for example, about 10 to about 30%, about 15 to about 25%, or about 18 to about 24% by weight of hydroxypropyl methylcellulose(s). In some embodiments, the formulation has about 20% by weight of one or more hydroxypropyl methylcelluloses. In further embodiments, the formulation has about 22% by weight of one or more hydroxypropyl methyl celluloses. Example hydroxypropyl methylcelluloses include Methocel K15M, Methocel K4M, and Methocel K100LV.

The sustained-release dosage forms of the invention can further include one or more fillers, glidants, disintegrants, binders, or lubricants as inactive ingredients. Fillers can be present in the formulations in an amount of 0 to about 85% by weight. In some embodiments, the formulation has about 50 to about 80%, about 55 to about 75%, or about 60 to about 70% by weight of filler. Non-limiting examples of fillers include lactose monohydrate, microcrystalline cellulose, starch 1500, and lactose anhydrous, or combinations thereof. In some embodiments, the filler comprises microcrystalline cellulose, lactose monohydrate, or both.

Lubricants can be present in the dosage forms of the invention in an amount of 0 to about 5% by weight. Non-limiting examples of lubricants include magnesium stearate, stearic acid (stearin), hydrogenated oil, polyethylene glycol, sodium stearyl fumarate, and glyceryl behenate. In some embodiments, the formulations include magnesium stearate, stearic acid, or both.

Glidants can be present in the dosage forms of the invention in an amount of 0 to about 5% by weight. Non-limiting examples of glidants include talc, colloidal silicon dioxide, and cornstarch. In some embodiments, the glidant is colloidal silicon dioxide.

Disintegrants can be present in the dosage forms of the invention in an amount of 0 to about 10% by weight. Non-limiting examples of disintegrants include croscarmellose sodium, crospovidone, starch, cellulose, and low substituted hydroxypropyl cellulose. Croscarmellose sodium is a preferred disintegrant.

Film-coating agents can be present in an amount of 0 to about 5% by weight. Non-limiting illustrative examples of film-coating agents include hypromellose or polyvinyl alcohol based coating with titanium dioxide, talc and optionally colorants available in several commercially available complete coating systems.

In some embodiments, the dosage form of the invention includes a sustained-release formulation comprising about 12.2% ruxolitinib phosphate, about 20% hydroxypropyl methylcellulose, about 64.3% filler, about 2.5% lubricant, and about 1% glidant, all by weight.

In some embodiments, the dosage form of the invention includes a sustained-release formulation comprising about 12.2% ruxolitinib phosphate, about 22% hydroxypropyl methylcellulose, about 62.3% filler, about 2.5% lubricant, and about 1% glidant, all by weight.

In some embodiments, the dosage form of the invention includes a sustained-release formulation as set out below.

| Component | Percentage (wt %) |
| --- | --- |
| Ruxolitinib phosphate | 12.2 |
| Microcrystalline cellulose, NF | 22.0 |
| Hypromellose, USP (Methocel K15M) | 4.0 |
| Hypromellose, USP (Methocel K4M) | 16.0 |
| Lactose monohydrate, NF | 42.3 |
| Colloidal silicon dioxide, NF | 1.0 |
| Magnesium stearate, NF | 0.5 |
| Stearic acid, NF | 2.0 |

In some embodiments, the dosage form of the invention includes a sustained-release formulation as set out below.

| Component | Percentage (wt %) |
| --- | --- |
| Ruxolitinib phosphate | 12.2 |
| Microcrystalline cellulose, NF | 42.3 |
| Hypromellose, USP (Methocel K100LV) | 10.0 |
| Hypromellose, USP (Methocel K4M) | 12.0 |
| Lactose monohydrate, NF | 20.0 |
| Colloidal silicon dioxide, NF | 1.0 |
| Magnesium stearate, NF | 0.5 |
| Stearic acid, NF | 2.0 |

In some embodiments, the dosage form of the invention includes a sustained-release formulation as set out below.

| Component | Percentage (wt %) |
| --- | --- |
| Ruxolitinib phosphate | 12.2 |
| Microcrystalline cellulose, NF | 22.0-42.3 |
| Hypromellose, USP (Methocel K100LV) | 0-10.0 |
| Hypromellose, USP (Methocel K15M) | 0-4.0 |
| Hypromellose, USP (Methocel K4M) | 12.0-16.0 |
| Lactose monohydrate, NF | 20.0-42.3 |
| Colloidal silicon dioxide, NF | 1.0 |
| Magnesium stearate, NF | 0.5 |
| Stearic acid, NF | 2.0 |

As used herein, the term "dosage form" is meant to refer to a physically discrete unit of sustained-release formulation of the invention to be administered to a patient. Example dosage forms include tablets, caplets, capsules, and the like, containing any of the sustained-release formulations described herein. Dosage forms can further include pharmaceutically acceptable coatings, pigments, or dyes.

The dosage forms of the invention contain a sustained-release formulation that results in the relatively slow release of ruxolitinib once administered, characterized by particular pharmacokinetic parameters different from those of an immediate-release formulation. The sustained-release dosage forms of the invention can minimize potentially harmful spikes in drug plasma concentrations that are associated with immediate-release formulations, and can help provide continuous, steady, and therapeutically effective plasma levels of drug. The dosage forms of the invention can be administered to a human patient as needed for therapeutic efficacy against the disease being treated, for example, once daily.

In some embodiments, the dosage forms of the invention are administered to fasted patients. As used herein, "fasted" means, in reference to a human patient or subject, that the patient or subject has not ingested food or drink (except water) for at least 3 hours prior to dosing. In some embodiments, patients are fasted for at least 10 hours prior to dosing.

In further embodiments, the dosage forms of the invention are administered to non-fasted human patients or subjects. Bioavailability of ruxolitinib is high (e.g., about 70-80%) and no food effect has been observed in immediate-release dosage forms. Accordingly, it is believed that the pharmacokinetics of ruxolitinib administered as a sustained-release dosage form would not be significantly different in fasted and non-fasted patients.

In some embodiments, administration of the sustained-release dosage form of the invention to a human results in a mean peak plasma concentration ($C_{max}$) of ruxolitinib of about 700 nM or less.

In some embodiments, administration of the sustained-release dosage form of the invention to a human results in a mean peak plasma concentration ($C_{max}$) of ruxolitinib of about 600 nM or less.

In some embodiments, administration of the sustained-release dosage form of the invention to a human results in a mean peak plasma concentration ($C_{max}$) of ruxolitinib of about 500 nM or less.

In some embodiments, administration of the sustained-release dosage form of the invention to a human results in a mean peak plasma concentration ($C_{max}$) of ruxolitinib of about 400 nM or less.

In some embodiments, administration of the sustained-release dosage form of the invention to a human results in a mean peak plasma concentration ($C_{max}$) of ruxolitinib of about 200 to about 700 nM.

In some embodiments, administration of the sustained-release dosage form of the invention to a human results in a mean peak plasma concentration ($C_{max}$) of ruxolitinib of about 200 to about 600 nM.

In some embodiments, administration of the sustained-release dosage form of the invention to a human results in a mean peak plasma concentration ($C_{max}$) of ruxolitinib of about 300 to about 500 nM.

In some embodiments, administration of the sustained-release dosage form of the invention to a human results in a mean peak plasma concentration ($C_{max}$) of ruxolitinib of about 300 to about 400 nM.

In some embodiments, administration of the sustained-release dosage form of the invention to a human results a mean time to peak plasma concentration ($T_{max}$) of ruxolitinib of about 1.5 hours or more.

In some embodiments, administration of the sustained-release dosage form of the invention to a human results in a mean time to peak plasma concentration ($T_{max}$) of ruxolitinib of about 1.5 hours to about 5 hours.

In some embodiments, administration of the sustained-release dosage form of the invention to a human results in a mean time to peak plasma concentration ($T_{max}$) of ruxolitinib of about 2 hours to about 4 hours.

In some embodiments, administration of the sustained-release dosage form of the invention to a human results in a ratio of mean peak plasma concentration ($C_{max}$) to mean 12-hour plasma concentration ($C_{12h}$) of ruxolitinib of about 10 or less.

In some embodiments, administration of the sustained-release dosage form of the invention to a human results in a ratio of mean peak plasma concentration ($C_{max}$) to mean 12-hour plasma concentration ($C_{12h}$) of ruxolitinib of about 6 or less.

In some embodiments, administration of the sustained-release dosage form of the invention to a human results in a ratio of mean peak plasma concentration ($C_{max}$) to mean 12-hour plasma concentration ($C_{12h}$) of ruxolitinib of about 5 or less.

In some embodiments, administration of the sustained-release dosage form of the invention to a human results in a ratio of mean peak plasma concentration ($C_{max}$) to mean 12-hour plasma concentration ($C_{12h}$) of ruxolitinib of about 4 or less.

In some embodiments, administration of the sustained-release dosage form of the invention to a human results in a ratio of mean peak plasma concentration ($C_{max}$) to mean 12-hour plasma concentration ($C_{12h}$) of ruxolitinib of about 1 to 10.

In some embodiments, administration of the sustained-release dosage form of the invention to a human results in a ratio of mean peak plasma concentration ($C_{max}$) to mean 12-hour plasma concentration ($C_{12h}$) of ruxolitinib of about 2 to 7.

In some embodiments, administration of the sustained-release dosage form of the invention to a human results in a mean half-life ($t_{1/2}$) of from about 3.5 hours to about 11 hours.

In some embodiments, administration of the sustained-release dosage form of the invention to a human results in a mean half-life ($t_{1/2}$) of from about 4 hours to about 8 hours.

In some embodiments, administration of a single dose of a sustained-release dosage form of the invention to a human results in mean bioavailability ($AUC_{0-\infty}$) of ruxolitinib of at least about 3000 nM*h.

In some embodiments, administration of a single dose of a sustained-release dosage form of the invention to a human results in mean bioavailability ($AUC_{0-\infty}$) of ruxolitinib of at least about 3500 nM*h.

In some embodiments, administration of a single dose of a sustained-release dosage form of the invention to a human results in mean bioavailability ($AUC_{0-\infty}$) of ruxolitinib of about 3000 to about 4000 nM*h.

In some embodiments, administration of a single dose of a sustained-release dosage form of the invention to a human results in mean bioavailability ($AUC_{0-\infty}$) of ruxolitinib of about 3100 to about 3800 nM*h.

In some embodiments, the sustained-release dosage form of the invention has a mean relative bioavailability based on AUC of from about 65% to about 110% or about 75% to about 95% relative to an immediate release formulation comprising the same amount of ruxolitinib, or a pharmaceutically acceptable salt thereof, in patients. AUC can be, for example, $AUC_{0-\infty}$ (e.g., for a single dose) or $AUC_{0-t}$ where t is a specified time.

As used herein, "mean" when preceding a pharmacokinetic value (e.g. mean $C_{max}$) represents the arithmetic mean value of the pharmacokinetic value taken from a population of patients unless otherwise specified.

As used herein, "$C_{max}$" means the maximum observed plasma concentration.

As used herein, "$C_{12h}$" refers to the plasma concentration measured at 12 hours from administration.

As used herein, "$T_{max}$" refers to the time at which the maximum blood plasma concentration is observed.

As used herein, "$T_{1/2}$" refers to the time at which the plasma concentration is half of the observed maximum.

As used herein, "AUC" refers to the area under the plasma concentration-time curve which is a measure of total bioavailability.

As used herein, "$AUC_{0-\infty}$" refers to the area under the plasma concentration-time curve extrapolated to infinity.

As used herein, "$AUC_{0-t}$" refers to the area under the plasma concentration-time curve from time 0 to the last time point with a quantifiable plasma concentration, usually about 12-36 hours.

As used herein, "$AUC_{0-\tau}$" refers to the area under the plasma concentration-time curve from time 0 to the time of the next dose.

As used herein, "Cl/F" refers to oral clearance.

The sustained-release dosage forms of the invention have certain advantages over immediate-release dosage forms. The maintenance of steady, therapeutically effective plasma levels of ruxolitinib afforded by the sustained-release dosage forms of the invention allows for reduced dosing, such as doing only once per day, as opposed to twice or more for immediate-release forms. The reduced dosing can help with patient compliance in their treatment regimen.

In some embodiments, administration of the sustained-release dosage form of the invention to a human results in a therapeutically effective plasma level of ruxolitinib for at least about 8 hours, at least about 10 hours, at least about 12 hours, at least about 18, or at least about 24 hours. In some embodiments, the sustained-release dosage form of the invention maintains a plasma level between about 75 and about 500 nM for at least about 8 hours, at least about 12 hours, or at least about 18 hours. In some embodiments, the sustained-release dosage form of the invention maintains a plasma level between about 100 and about 400 nM for at least about 6 hours or at least about 8 hours.

An additional advantage of the sustained-release dosage form (e.g., containing 25 mg of ruxolitinib phosphate on a free base basis) includes a reduction in unwanted side effects related to thrombocytopenia and anemia while maintaining therapeutic efficacy comparable with an immediate-release dosing regimen, e.g., 15 mg or 20 mg BID. It was not predictable that a sustained-release formulation of ruxolitinib could both maintain therapeutic efficacy and significantly reduce unwanted side effects related to thrombocytopenia or reduced hemoglobin levels. Clinical data related to efficacy and side effects in myelofibrosis patients for both sustained-release and immediate-release dosing is compared in the Examples.

In some embodiments, administration of the sustained-release dosage form of the invention to a human once daily for at least 16 weeks results in a mean decrease in mean base platelet count of no more than about $100 \times 10^9/L$, no more than about $80 \times 10^9/L$, no more than about $60 \times 10^9/L$, or no more than about $40 \times 10^9/L$.

In some embodiments, administration of the sustained-release dosage form of the invention to a human once daily for at least 16 weeks results in a mean decrease in mean base platelet count of between about $0 \times 10^9/L$ and about $100 \times 10^9/L$, between about $30 \times 10^9/L$ and about $80 \times 10^9/L$, or between about $50 \times 10^9/L$ and about $70 \times 10^9/L$.

In some embodiments, administration of the sustained-release dosage form of the invention to a human once daily for at least 16 weeks results in a mean decrease in mean baseline hemoglobin (Hgb) of no more than about 15 g/L, no more than about 10 g/L, no more than about 8 g/L, or no more than about 6 g/L.

In some embodiments, administration of the sustained-release dosage form of the invention to a human once daily for at least 16 weeks results in a mean decrease in mean baseline hemoglobin (Hgb) of about 0 to about 15 g/L, about 5 to about 15 g/L, about 2 to about 12 g/L, or about 5 to about 12 g/L.

In some embodiments, the platelet counts and hemoglobin levels are measured in patients having received no blood transfusions during the treatment period.

Mean baseline platelet counts and mean baseline hemoglobin levels are typically measured prior to the start of treatment.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Methods

Another aspect of the present invention pertains to methods of treating a JAK-associated disease or disorder in an individual (e.g., patient) by administering to the individual in need of such treatment a sustained-release dosage form of the invention. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chondrolysis, chondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

The present invention further provides methods of treating psoriasis or other skin disorders by administration of a topical formulation containing a compound of the invention.

In some embodiments, sustained-release formulation and dosage forms described herein can be used to treat pulmonary arterial hypertension.

In some embodiments, the sustained-release formulation and dosage forms described herein can be used to treat mast cell activation syndrome.

The present invention further provides a method of treating dermatological side effects of other pharmaceuticals by administration of the sustained-release dosage form of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The dosage form of the invention can be administered in combination with (e.g., simultaneously or sequentially) the pharmaceutical agent having the undesirable dermatological side effect.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The sustained-release dosage forms herein can further be used to treat ischemia reperfusion injuries or a disease or condition related to an inflammatory ischemic event such as stroke or cardiac arrest. The sustained-release dosage forms described herein can further be used to treat endotoxin-driven disease state (e.g., complications after bypass surgery or chronic endotoxin states contributing to chronic cardiac failure). The sustained-release dosage forms described herein can further be used to treat anorexia, cachexia, or fatigue such as that resulting from or associated with cancer. The sustained-release dosage forms described herein can further be used to treat restenosis, sclerodermitis, or fibrosis. The sustained-release dosage forms described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390 (Pt 2):427-36 and Sriram, K. et al. *J. Biol. Chem.* 2004, 279(19):19936-47. Epub 2004 Mar. 2, both of which are incorporated herein by reference in their entirety. The sustained-release dosage forms described herein can be used to treat Alzheimer's disease.

The sustained-release dosage forms described herein can further be used to treat other inflammatory diseases such as systemic inflammatory response syndrome (SIRS) and septic shock.

The sustained-release dosage forms described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, sustained-release dosage forms described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface,* 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the sustained-release dosage forms of the invention, optionally in combination with other JAK inhibitors such as those reported in U.S. Ser. No. 11/637,545, which is incorporated herein by reference in its entirety, can be used to treat respiratory dysfunction or failure associated with viral infection, such as influenza and SARS.

As used herein, the term "individual," "subject," or "patient," refers to a human, who can be fasted or un-fasted when the dosage form of the invention is administered.

As used herein the term "pharmaceutically acceptable" refers to those compounds, materials, compositions and/or dosage forms, which are, within the scope of sound medical judgment, suitable for contact humans without excessive toxicity, irritation, allergic response and other problem complications commensurate with a reasonable benefit/risk ratio.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the sustained-release dosage forms described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of sustained-release dosage forms with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an anti-metabolite/demethylating agent (e.g., 5-flurouracil, capecitabine or azacitidine); an anti-hormone therapy (e.g., hormone receptor antagonists, SERMs, or aromotase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Example 1

Sustained-Release and Immediate-Release Formulations of Ruxolitinib Phosphate

Formulation SR-2

A 25 mg sustained-release formulation of ruxolitinib phosphate was prepared according to the following protocol. The formulation components are provided in Table 1a. Percentages are by weight.

TABLE 1a

| Component | Function | Percentage |
|---|---|---|
| Ruxolitinib phosphate[a] | Active ingredient | 12.2 |
| Microcryrstalline cellulose, NF | Filler | 22.0 |
| Hypromellose, USP (Methocel K15M) | Sustained release matrix former | 4.0 |
| Hypromellose, USP (Methocel K4M) | Sustained release matrix former | 16.0 |
| Lactose monohydrate, NF | Filler | 42.3 |
| Colloidal silicon dioxide, NF | Glidant | 1.0 |
| Magnesium stearate, NF | Lubricant | 0.5 |
| Stearic acid, NF | Lubricant | 2.0 |
| Total | | 100 |

[a]On a free base basis, conversion factor for phosphate salt to free base is 0.7575.

Protocol

Step 1. Add microcrystalline cellulose, ruxolitinib phosphate, lactose monohydrate, and hypromelloses to a suitable blender and mix.
Step 2. Transfer the mix from Step 1 to a suitable granulator and mix.
Step 3. Add purified water while mixing.
Step 4. Screen the wet granules from Step 3.
Step 5. Transfer the granules from Step 4 into a suitable dryer and dry until LOD is no more than 3%.
Step 6. Screen the granules from Step 5.
Step 7. Mix colloidal silicon dioxide with granules in Step 6 in a suitable blender.
Step 8. Mix stearic acid and magnesium stearate with the blend in Step 7 and continue blending.
Step 9. Compress the final blend in Step 8 on a suitable rotary tablet press.

Formulation SR-1

An alternate 25 mg sustained-release formulation of ruxolitinib phosphate has been prepared as described below. The formulation components are provided in Table 1b. Percentages are by weight.

TABLE 1b

| Component | Function | Percentage |
|---|---|---|
| Ruxolitinib phosphate[a] | Active ingredient | 12.2 |
| Microcryrstalline cellulose, NF | Filler | 42.3 |
| Hypromellose, USP (Methocel K100LV) | Sustained release matrix former | 10.0 |
| Hypromellose, USP (Methocel K4M) | Sustained release matrix former | 12.0 |

TABLE 1b-continued

| Component | Function | Percentage |
|---|---|---|
| Lactose monohydrate, NF | Filler | 20.0 |
| Colloidal silicon dioxide, NF | Glidant | 1.0 |
| Magnesium stearate, NF | Lubricant | 0.5 |
| Stearic acid, NF | Lubricant | 2.0 |
| Total | | 100 |

[a] On a free base basis, conversion factor for phosphate salt to free base is 0.7575.

Protocol

Step 1. Add microcrystalline cellulose, ruxolitinib phosphate, lactose monohydrate, and hypromelloses to a suitable blender and mix.
Step 2. Transfer the mix from Step 1 to a suitable granulator and mix.
Step 3. Add purified water while mixing.
Step 4. Screen the wet granules from Step 3.
Step 5. Transfer the granules from Step 4 into a suitable dryer and dry until LOD is no more than 3%.
Step 6. Screen the granules from Step 5.
Step 7. Mix colloidal silicon dioxide with granules in Step 6 in a suitable blender.
Step 8. Mix stearic acid and magnesium stearate with the blend in Step 7 and continue blending.
Step 9. Compress the final blend in Step 8 on a suitable rotary tablet press.

Formulation C—Immediate Release

Immediate-release dosage forms of ruxolitinib phosphate can be obtained commercially in 5, 10, 15, 20, and 25 mg doses as the drug product Jakafi® (ruxolitinib phosphate (tablets)) (NDA no. N202192). The commercially available dosage forms are the same as used in the Phase 3 COMFORT-1 and COMFORT-II studies.

Example 2

Bioavailability Study of Sustained Release Formulation

A relative bioavailability study of the sustained release and immediate formulations of ruxolitinib phosphate was conducted in healthy adult volunteers. Subjects in the fasted state were given a single oral dose of immediate-release formulation (25 mg, see Example 1) or a single oral dose of sustained-release formulation (25 mg, see Example 1). Plasma concentrations of ruxolitinib were measured and are compared in FIG. 1. Table 2a provides comparative pharmacokinetic (PK) data.

Description of Bioavailability Study

This study was performed to evaluate pharmacokinetic performance of two ruxolitinib phosphate sustained release (SR) formulations compared to the ruxolitinib phosphate immediate release (IR) tablets. The study was conducted as a 3-period study in which each subject received the IR tablets, the SR-1 tablets and the SR-2 tablets, all in fasted state. All treatments were administered as a single dose in one tablet. Nine healthy subjects enrolled in this study received IR tablets in Period 1, and 8 subjects continued on the study were randomized into 2 sequences to receive SR-1 and SR-2 tablets in Period 2 and Period 3.

The 9 subjects enrolled in the study received a single dose of IR tablets, SR-1 tablets and SR-2 tablets, according to the randomization schedule (see Table 2b). Dosing was administered orally after at least 10 hour overnight fast, and a standardized meal was served approximately 3 hours after administration. A washout period of 7 days (not less than 5 days) was instituted between the treatment periods.

Blood samples for determination of plasma concentrations of ruxolitinib were collected at 0, 0.25, 0.5, 1, 1.5, 2, 3, 4, 6, 8, 12, 16, 24 and 36 hours post-dose using lavender top (K2EDTA) Vacutainer® tubes. No samples were collected for determination of urine concentrations of ruxolitinib.

TABLE 2b

Randomization Schedule for Study

| Sequence | Period 1 | Period 2 | Period 3 | Subject |
|---|---|---|---|---|
| 1 | 25 mg IR tablet fasted | 25 mg SR-1 tablet fasted | 25 mg SR-2 tablet fasted | 102*, 103, 106, 107, 109 |
| 2 | 25 mg IR tablet fasted | 25 mg SR-2 tablet fasted | 25 mg SR-1 tablet fasted | 101, 104, 105, 108 |

*Subject withdrew from the study before the start of Period 2

Plasma and urine samples were shipped to Incyte Corporation for determination of ruxolitinib concentrations. The plasma samples were assayed by validated, GLP, LC/MS/MS methods with a linear range of 1 to 1000 nM.

All PK blood samples were collected within 5 minutes of their scheduled time, and therefore the schedule times relative to the time of dose administration were used for all pharmacokinetic analyses.

Standard non-compartmental pharmacokinetic methods were used to analyze the ruxolitinib plasma concentration data using Phoenix WinNonlin version 6.0 (Pharsight Cor- TABLE 2a*

| Treatment | n | $C_{max}$ (nM) | $T_{max}$ (h) | $C_{12\,h}$ (nM) | $C_{max}/C_{12\,h}$ | $t_{1/2}$ (h) | $AUC_{0\text{-}t}$ (nM * h) | $AUC_{0\text{-}\infty}$ (nM * h) | Cl/F (L/h) |
|---|---|---|---|---|---|---|---|---|---|
| 25 mg IR | 9 | 1100 ± 332 1060 | 0.94 ± 0.46 0.86 | 45.6 ± 38.1 32.1 | 40 ± 24 33 | 2.8 ± 0.72 2.7 | 4340 ± 1990 3930 | 4350 ± 1990 3940 | 22.8 ± 10.3 20.7 |
| 25 mg SR-1 | 8 | 333 ± 76.1 325 | 2.4 ± 0.98 2.2 | 121 ± 46.8 114 | 3.0 ± 1.0 2.9 | 5.3 ± 1.8 5.1 | 3110 ± 840 3020 | 3180 ± 864 3090 | 27.2 ± 6.72 26.4 |
| 25 mg SR-2 | 8 | 394 ± 126 377 | 2.9 ± 1.6 2.5 | 104 ± 43.2 96.5 | 4.7 ± 3.1 3.9 | 6.1 ± 2.1 5.8 | 3520 ± 1260 3330 | 3740 ± 1400 3520 | 24.6 ± 9.02 23.2 |
| P-Values from a Crossover ANOVA of Log-Transformed Data | | | | | | | | | |
| | | <0.0001 | 0.0003 | — | — | <0.0001 | 0.040 | 0.070 | 0.070 |
| Geometric Mean Relative Bioavailability and 90% CI (Reference = IR) | | | | | | | | | |
| SR-1 vs. IR | | 30.4% 25.4-36.4% | | | | | 74.7% 62.2-89.7% | 76.2% 63.1-92.0% | |
| SR-2 vs. IR | | 35.2% 29.5-42.2% | | | | | 82.5% 68.7-99.1% | 86.7% 71.8-105% | |

*PK values are provided as mean ± SD and geometric mean poration, Mountain View, Calif.). Thus, $C_{max}$ and $T_{max}$ were taken directly from the observed plasma concentration data. The absorption lag time ($T_{lag}$) was defined as the sampling time immediately preceding that corresponding to the first measurable (non-zero) concentration. The terminal-phase disposition rate constant ($\lambda_z$) was estimated using a log-linear regression of the concentration data in the terminal disposition phase, and $t_{1/2}$ was estimated as $\ln(2)/\lambda_z$. $AUC_{0-t}$ was estimated using the linear trapezoidal rule for increasing concentrations and the log-trapezoidal rule for decreasing concentrations, and the total $AUC_{0-\infty}$ was calculated as $AUC_{0-t}+C_t/\lambda_z$. The oral-dose clearance (Cl/F) was estimated as $Dose/AUC_{0-\infty}$, and the terminal-phase volume of distribution ($V_z/F$) was estimated as $Dose/[AUC_{0-\infty}*\lambda_z]$.

The log-transformed pharmacokinetic parameters were compared among the treatments using a 2-factor ANOVA with the fixed factor for treatment and random factor for subject. The relative bioavailability of the fasted administration of the SR formulations (test treatments) compared to fasted administration of the IR tablets (reference treatment) were estimated using the geometric mean relative bioavailability and 90% confidence intervals for $C_{max}$, $AUC_{0-t}$ and $AUC_{0-\infty}$, which were calculated from the adjusted means (least square means) from the ANOVA. All statistical analyses were performed using SAS version 9.1 (SAS Institute, Inc., Cary, N.C.).

Example 3

Sustained-Release Clinical Trial

A Phase 2 clinical trial was carried out in patients with myelofibrosis (MF). A total of 41 subjects were enrolled, and spleen volume and total symptom scores were obtained at baseline. Tablets of sustained-release formulation SR-2 (see Example 1) were administered to fasted patients. All patients were treated with 25 mg once daily doses for 8 weeks. After 8 weeks, depending upon the clinical response, the investigator was allowed to (a) maintain the same dose of SR-2, (b) increase the dose to 50 mg once daily, (c) increase the dose to alternating doses of 25 mg and 50 mg, dosed once daily, or (d) switch to treatment with the immediate release formulation.

Figure 2:
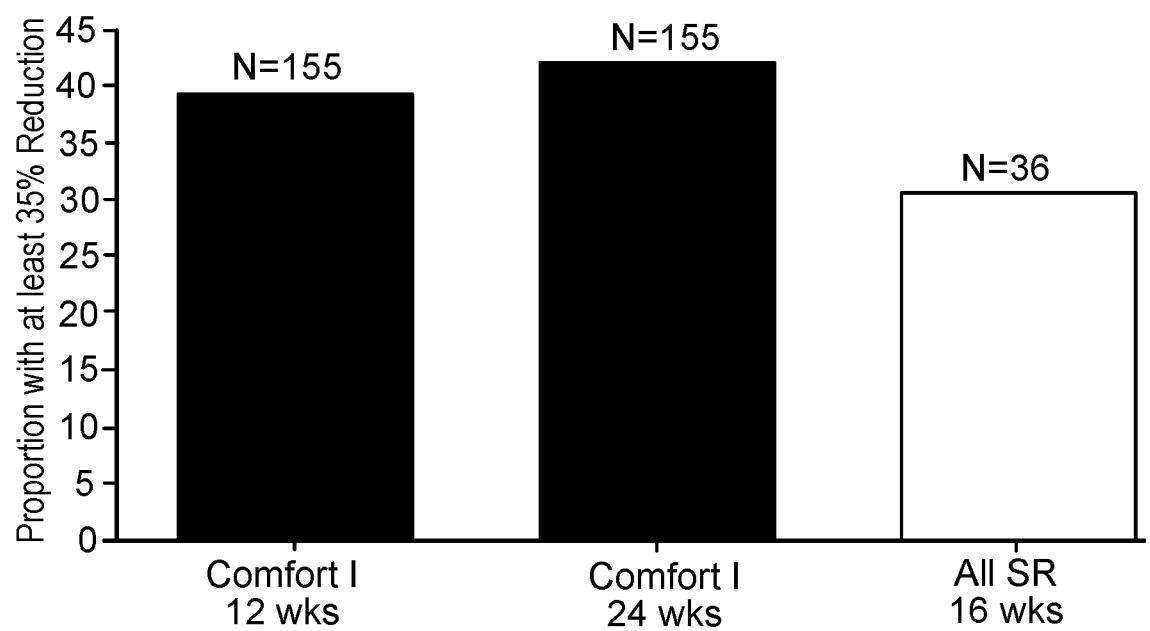
FIG. 2 shows a graph comparing spleen volume responders in the COMFORT-I immediate-release formulation study and the sustained-release study.
Figure 3:
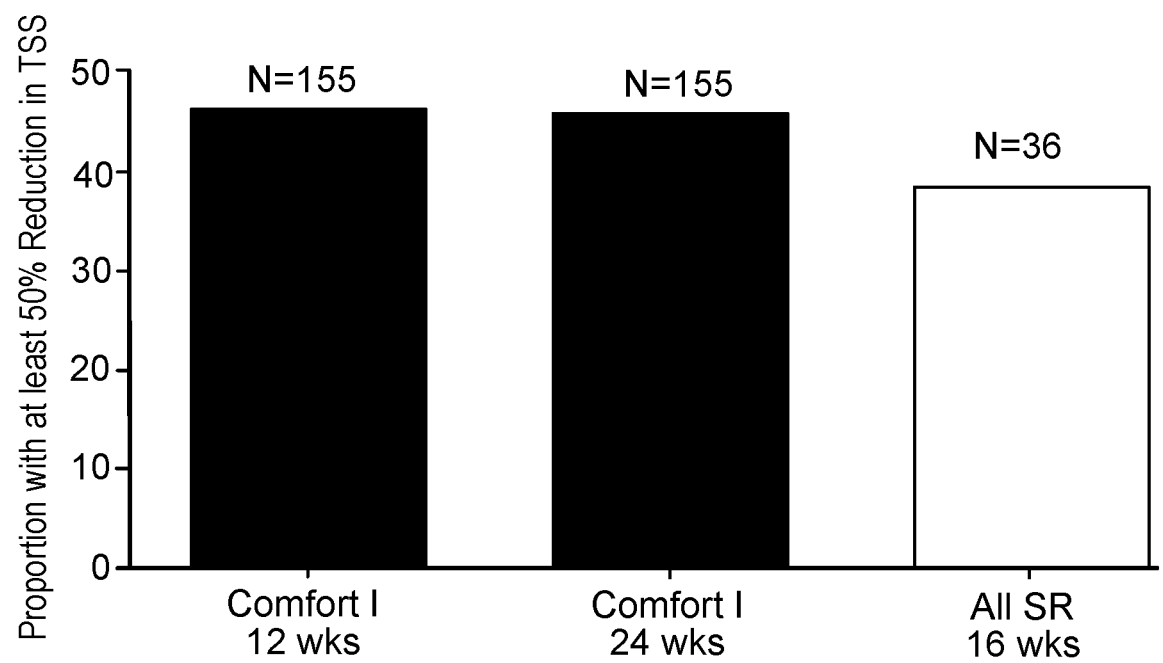
FIG. 3 shows a graph comparing total symptom scores in the COMFORT-I immediate-release formulation study and the sustained-release study.

Data related to spleen volume and total symptom scores are provided in FIGS. 2 and 3 together with comparative data from the COMFORT-1 Study where patients were dosed only with the immediate-release formulation. See Example A below for details of the COMFORT-1 Study. As can be seen in FIGS. 2 and 3, treatment with the 25 mg sustained-release formulation was nearly as effective as the immediate-release formulation in the COMFORT-I study. Percentages of spleen volume responders in COMFORT-1 as shown in FIG. 2 were 39.4% and 43.9% at 12 weeks and 24 weeks, respectively. The percentage of spleen volume responders in the sustained-release study at week 16 was 28.9%. Similarly, the percentages of total symptom score responders in COMFORT-1 as shown in FIG. 3 were 46.3% and 45.9% at 12 weeks and 24 weeks, respectively. The percentage of total symptom score responders in the sustained release study as shown in FIG. 3 was 36.8%.

Data relating to mean platelet count and mean hemoglobin levels (Hgb) is presented below in Table 3 together with comparative data from the COMFORT-I study. As can be seen from the data, the mean change from baseline platelet count in the SR patients was about half of what was observed in COMFORT-I. Similar results are seen for hemoglobin levels. Data is shown as mean±SD.

TABLE 3

| Parameter | Sustained-Release Study | COMFORT-I Study (active) | COMPFORT-I Study (placebo) |
|---|---|---|---|
| N | 41 | 155 | 154 |
| Mean Baseline platelet count, ×10$^9$/L | 274 ± 193 | 321 ± 202 | 280 ± 152 |
| Mean Baseline Hgb in patient with no transfusions, g/L | 105 ± 17 | 108 ± 20 | 106 ± 22 |
| | Week 16 | Week 12 | Week 12 |
| Mean total daily dose, mg | 34 | 30.4 | 0 |
| Mean change from baseline platelet count, ×10$^9$/L | −65 ± 101 | −131 ± 143 | −9 ± 75 |
| Mean change from baseline Hgb, g/L | −7.4 ± 13.3 | −13.2 ± 15.5 | 0.3 ± 11.5 |

Example 4

Figure 4:
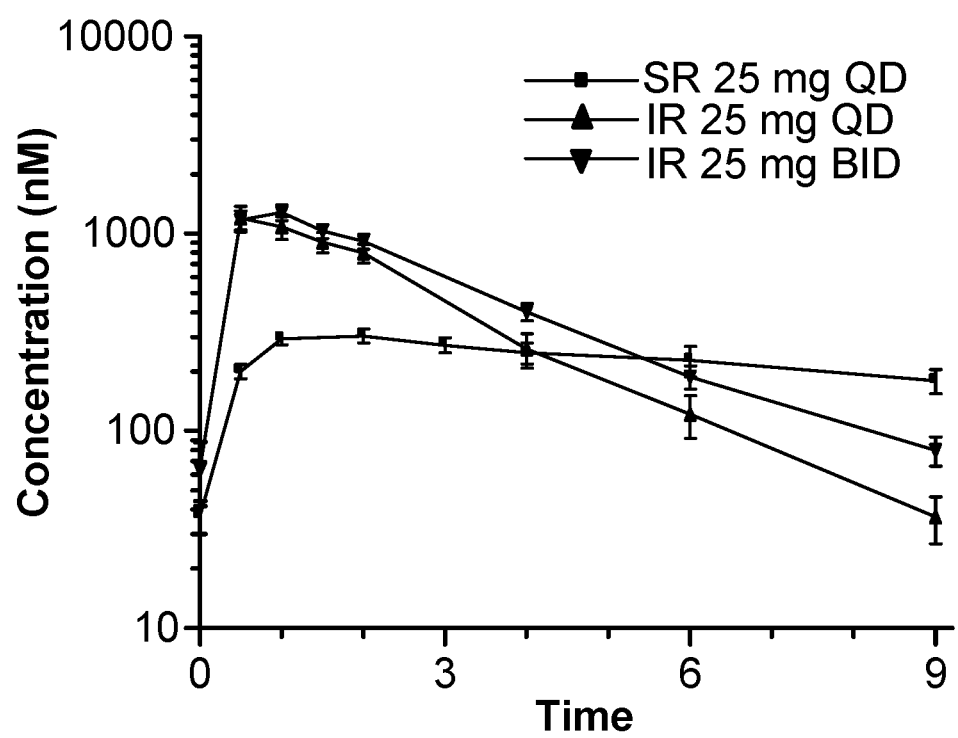
FIG. 4 shows a graph comparing ruxolitinib steady state plasma concentrations in MF patients dosed with 25 mg immediate-release or 25 mg sustained-release formulations.

Comparison of Steady State Plasma Concentrations of Ruxolitinib Between SR and IR Formulations in MF Patients Steady state plasma concentrations of ruxolitinib in myelofibrosis (MF) patients receiving repeating 25 mg doses are compared in FIG. 4 between sustained release (SR) and immediate release (IR) formulations. Comparative pharmacokinetic parameters are provided below in Table 4a.

TABLE 4a*

| Formula and Regimen | n | $C_{max}$ (nM) | $T_{max}$ (h) | $C_{min}$ (nM) | $t_{1/2}$ (h) | $AUC_{0-\tau}$ (nM * h) | $AUC_{0-t}$ (nM * h) | Cl/F (L/h) |
|---|---|---|---|---|---|---|---|---|
| SR 25 mg QD[a] | 39 | 397 ± 175 368 | 2.35 ± 1.75 1.88 | 32 ± 40.6 — | 7.33 ± 3.73 6.42 | 3650 ± 2450 3020 | 2060 ± 1140 1810 | 32.0 ± 18.0 27.1 |
| IR 25 mg BID[b] (1A) | 27 | 1481 ± 575 1374 | 0.83 ± 0.45 0.74 | 47 ± 54 — | 1.94 ± 0.50 1.88 | 4363 ± 2066 3949 | 4148 ± 1885 3778 | 22.7 ± 10.1 20.7 |
| IR 25 mg QD[b] (2A) | 6 | 1417 ± 150 1410 | 0.84 ± 0.38 0.78 | 0 ± 0 — | 1.60 ± 0.36 1.57 | 3567 ± 777 3494 | 3291 ± 604 3243 | 23.9 ± 5.5 23.4 |
| IR 25 mg BID[b] (2C) | 7 | 1650 ± 506 1578 | 0.79 ± 0.49 0.68 | 85 ± 102 43 | 1.96 ± 0.59 1.90 | 4939 ± 2566 4463 | 4444 ± 1918 4120 | 19.9 ± 8.1 18.3 |
| SR 25 mg single dose[c] | 8 | 394 ± 126 377 | 2.9 ± 1.6 2.5 | — | 6.1 ± 2.1 5.8 | 3740 ± 1400 3520 | — | 24.6 ± 9.02 23.2 |

[a]From SR study described in Example 3
[b]From IR study described below (Description of Open-Label Study in MF patients)
[c]From single dose study described in Example 2 ($AUC_{0-\tau}$ will be $AUC_{0-\infty}$)
*Values are mean ± SD and geometric mean.

Description of Open-Label Study in MF Patients
General Description

This was an open-label study exploring the safety, tolerability, and efficacy of ruxolitinib, administered orally to patients with primary myelofibrosis (PMF) and post polycythemia vera/essential thrombocythemia myelofibrosis (Post-PV/ET MF). The study was comprised of 3 parts: Part 1—dose escalation and expansion, bid dosing, Part 2—alternative dosing schedules (A, B and C), and Part 3—three independent patient groups (Group I, II and III). Eight dose regimens were evaluated in 3 parts. The Part 1 evaluated two dose levels of 25 mg bid and 50 mg bid, Part 2 studied five dose regimens of 10 mg bid, 25 mg bid, 25 mg qd, 50 mg qd and 100 mg qd and Part 3 assessed six dose regimens of 10 mg bid, 15 mg bid, 25 mg bid, 50 mg qd, 100 mg qd and 200 mg qd. A total of 154 subjects were enrolled; 32 subjects enrolled in Part 1, 29 subjects in Part 2 and 93 subjects in Part 3. See Table 4b (qd=once per day; bid=twice per day).

In Part 1, the pharmacokinetic blood samples were collected at pre-dose and 0.5, 1, 1.5, 2, 4, 6 and 9 hours post-dose on Days 1 and 15 of Cycle 1 and at pre-dose on Day 1 of Cycles 2 and 3, using lavender top (K3EDTA) Vacutainer® tubes. In Part 2, the pharmacokinetic samples were collected at pre-dose and 0.5, 1, 1.5, 2, 4, 6 and 9 hours post-dose on Day 15 of Cycle 1 and at pre-dose on Day 1 of Cycles 2 and 3. In Part 3, the pharmacokinetic samples were collected at pre-dose and 2 hours after administration of the morning dose of ruxolitinib on Day 15 of Cycle 1 and Day 1 of Cycles 2 and 3.

Plasma concentration data from Cycle 1 for subjects in Part 1 and 2 were used for non-compartmental analysis while all plasma concentration data were used for population PK analysis.

Following fasting, oral, first-dose or multiple-dose administration of ruxolitinib phosphate tablets, the drug was absorbed rapidly, typically attaining peak plasma concentrations within 0.3 to 2 hours after administration in all subjects. Plasma concentrations subsequently declined in a monophasic or biphasic fashion.

The mean $C_{max}$ and AUC increased approximately linearly proportional to dose from 10 mg to 100 mg. The pharmacokinetics of ruxolitinib in MF patients was similar to that in healthy volunteers.

Detailed Description of Clinical Trial

This multicenter, open-label, non-randomized, dose escalation clinical study was conducted by M. D. Anderson Cancer Center, Houston, Tex. and Mayo Clinic, Rochester, Minn., according to Protocol INCB 18424-251, and 154 patients with PMF or Post-PV/ET MF were enrolled and received at least a single dose according to the study plan in Table 4b. The study was comprised of 3 parts: Part 1—dose escalation and expansion cohort, bid dosing, Part 2—alternative dosing schedules (A, B and C), and Part 3—three independent patient groups (Group I, II and III). Schedules A, B and C in Part 2 were once daily (qd) dosing regimens, low dose regimen of 10 mg bid and induction/maintenance regimen, respectively. Part 3 was studied in three separate groups of patients to further evaluate the safety and efficacy of selected starting dose levels and to explore dose modification on an individual patient basis as appropriate. Dose hold and withdrawal for safety were defined in terms of platelet count and absolute neutrophil count (ANC) while provision for dose increase was provided based on inadequate efficacy defined by change in spleen size.

Ruxolitinib phosphate tablets (5 and 25 mg) were administered as oral doses with water in an outpatient setting. Doses ranged from 10 mg bid to 50 mg bid, and from 25 mg qd to 200 mg qd. The individual patient participation was expected to be approximately 12-24 months; patients might continue on therapy indefinitely if they did not meet any of the withdrawal criteria, did not have disease progression and are receiving some clinical benefit.

In Part 1, the pharmacokinetic blood samples were collected at pre-dose and 0.5, 1, 1.5, 2, 4, 6 and 9 hours post-dose on Days 1 and 15 of Cycle 1 and at pre-dose on Day 1 of Cycles 2 and 3, using lavender top (K3EDTA) Vacutainer® tubes. In Part 2, the pharmacokinetic samples were collected at pre-dose and 0.5, 1, 1.5, 2, 4, 6 and 9 hours post-dose on Day 15 of Cycle 1 and at pre-dose on Day 1 of Cycles 2 and 3. In Part 3, the pharmacokinetic samples were collected at pre-dose and 2 hours after administration of the morning dose on Day 15 of Cycle 1 and Day 1 of Cycles 2 and 3.

TABLE 4b

| Part | Schedule | Dose Regimen |
|---|---|---|
| 1 | A | 25 mg bid |
| 1 | B | 50 mg bid |
| 2 | A | 25 mg qd |
| 2 | A | 50 mg qd |
| 2 | A | 100 mg qd |
| 2 | B | 10 mg bid |
| 2 | C | 25 mg bid |
| 3 | I | 50 mg qd |
| 3 | I | 10 mg qd |
| 3 | I | 25 mg bid |
| 3 | II | 100 mg qd |
| 3 | II | 200 mg qd |
| 3 | III | 10 mg bid |
| 3 | III | 15 mg bid |

Plasma samples were shipped to Incyte Corporation and assayed by a validated, GLP, LC/MS/MS method with a linear range of 1 to 1000 nM and a limit of quantification of 1 nM.

Generally, the actual time post-dose was used for pharmacokinetic analyses. However, the dose information on Cycle 1 Day 15 for patients in Part 2 and three additional patients in Part 1 were not collected. The nominal time were used for pharmacokinetic analyses for these patients. The dose information on Cycle 1 Day 15 for four additional patients were questionable. Hence, the nominal time were used for these patients also. Plasma concentrations at 12 hours post dose for bid or 24 hours post dose for qd on Cycle 1, Day 15 were imputed by sample at pre-dose on Cycle 1 Day 15 to calculate steady state $AUC_{0-\tau}$.

Standard noncompartmental pharmacokinetic methods were used to analyze the ruxolitinib plasma concentration data using WinNonlin version 6.0 (Pharsight Corporation, Mountain View, Calif.). Thus, $C_{max}$ and $T_{max}$ were taken directly from the observed plasma concentration data. For single dose, the terminal-phase disposition rate constant ($\lambda_z$) was estimated using a log-linear regression of the concentration data in the terminal disposition phase, and $t_{1/2}$ was estimated as $\ln(2)/\lambda_z$. $AUC_{0-t}$ was estimated using the linear-trapezoidal rule for increasing concentrations and the log-trapezoidal rule for decreasing concentrations, and the total $AUC_{0-\infty}$ was calculated as $AUC_{0-t}+C_t/\lambda_z$. The oral-dose clearance (Cl/F) was estimated as Dose/$AUC_{0-\infty}$, and the terminal-phase volume of distribution ($V_z/F$) was estimated as Dose/[$AUC_{0-\infty}*\lambda_z$].

For the multiple-dose data, $\lambda_z$ was estimated using a log-linear regression of the concentration data in the terminal disposition phase, and $t_{1/2}$ was estimated as $\ln(2)/\lambda_z$. The AUC over one dosing interval ($AUC_{0-12h}$ for q12h administration, or $AUC_{0-24h}$ for q24h administration) was estimated using the linear trapezoidal rule for increasing concentrations and the log-trapezoidal rule for decreasing concentrations. The Cl/F was estimated as Dose/AUC, and $V_z/F$ was estimated as Dose/[AUC*$\lambda_z$]. Additionally, the $C_{min}$ and $AUC_{0-t}$(Area under the steady-state plasma concentration-time curve from time zero to the time of the last sample obtained) were calculated for the multiple-dose data.

The PK parameters of ruxolitinib were summarized for each dose group using descriptive statistics, and the log-transformed ruxolitinib PK parameters were compared among the dose groups using a 1-factor analysis of variance. The dose-proportionality of $C_{max}$ and AUC was evaluated using a power function regression model (eg, $C_{max}=\alpha \cdot Dose\beta$).

The pharmacokinetics of ruxolitinib in MF patients was similar to that in healthy volunteers.

Example 5

Comparative Efficacy of Sustained Release and Immediate Release Formulations

Enlarged spleen is a common and prominent symptom of myelofibrosis. Reduction in spleen volume serves as a measure for assessing the effectiveness of a given treatment. Table 5a reports the mean reduction in spleen volume in MF patients enrolled in the sustained-release study (See Example 3) at 16 weeks of treatment, while Table 5b reports the mean reduction in spleen volume in MF patients enrolled in the COMFORT-I study (immediate release, see Comparative Example A) at 24 weeks of treatment. As can be seen from the data, both the sustained-release and immediate release treatment regimens were effective in reducing spleen volume.

TABLE 5a

Spleen Volume (cm³) from Sustained-Release Study

Percent Change from Baseline to Week 16 (%)

| | |
|---|---|
| n | 40 |
| Mean | −22.3 |
| STD | 20.79 |
| Median | −21.7 |
| (MIN, MAX) | (−64.6, 43.6) |

TABLE 5b

Spleen Volume (cm³) from COMFORT I (Immediate-Release)

| | Treatment Group | | | |
|---|---|---|---|---|
| | To Week 12 (%) | | To Week 24 (%) | |
| Percent Change from Baseline | Ruxolitinib (N = 155) | Placebo (N = 154) | Ruxolitinib (N = 155) | Placebo (N = 154) |
| n | 148 | 132 | 139 | 106 |
| Mean | −32.0 | 8.4 | −31.6 | 8.1 |
| STD | 15.58 | 14.61 | 18.92 | 15.31 |
| Min | −74.4 | −26.2 | −75.9 | −46.4 |
| Median | −31.7 | 6.1 | −33.0 | 8.5 |
| Max | 3.8 | 64.6 | 25.1 | 48.8 |

Effectiveness of a treatment regimen in an MF patient can also be assessed by Total Symptom Score. In calculating Total Symptom Score, symptoms of MF were assessed using a symptom diary (modified MFSAF v2.0 diary) where subjects recorded answers to queries regarding MF symptoms on a handheld device. Symptoms assessed included filling up quickly/early satiety, abdominal discomfort, abdominal pain, inactivity, night sweats, itching, and bone/muscle pain.

Table 5c reports the Total Symptom Score results in the sustained-release study (see Example 3) while Table 5d reports the Total Symptom Score results in the COMFORT-I study (immediate-release, see Comparative Example A) at 24 weeks. As can be seen from the data, both the SR and IR regimens were effective at treating MF in patients.

TABLE 5c

Total Symptom Scores from Sustained-Release Study

Percent Change from Baseline to Week 16

| | |
|---|---|
| n | 38 |
| Mean | −50.4 |
| STD | 31.16 |
| Median | −48.6 |
| (MIN, MAX) | (−100.0, 12.7) |

TABLE 5d

Total Symptom Score from COMFORT I Study (Immediate-Release)

| | Treatment Group | | | |
|---|---|---|---|---|
| | Ruxolitinib To Week 16 | Placebo To Week 16 | Ruxolitinib To Week 24 | Placebo To Week 24 |
| Percent Change from Baseline | (N = 155) | (N = 154) | (N = 155) | (N = 154) |
| n | 140 | 124 | 129 | 103 |
| Mean | −40.5 | 37.8 | −46.1 | 41.8 |
| STD | 54.31 | 93.92 | 48.55 | 99.26 |
| Min | −100.0 | −82.5 | −100.0 | −100.0 |
| Median | −51.1 | 12.7 | −56.2 | 14.6 |
| Max | 292.5 | 464.8 | 108.3 | 511.6 |

Example 6

Comparison of Adverse Events in Patients Enrolled in the Sustained-Release Study and COMFORT-I (Immediate-Release) Study Data for adverse events relating to anemia, thrombocytopenia, neutropenia, and all Grade 3 or higher adverse events are compared for the sustained-release and COMFORT-I (immediate-release) studies (see Example 3 and Comparative Example A for descriptions of the studies) in Table 6a. Adverse events are graded according to CTCAE criteria which can be found online at ctep.cancer.gov/protocolDevelopment/electronic_applications/ctc.htm or evs.nci.nih.gov/ftp1/CTCAE/CTCAE_4.03_2010-06-14_Quick-Reference_5×7.pdf. A Grade 3 adverse event generally corresponds to a reaction that is severe or medically significant, but not immediately life-threatening where hospitalization or prolongation of hospitalization is indicated and where the reaction is disabling to the extent of limiting self care. Higher Grades are 4 (life-threatening requiring urgent intervention) and 5 (death). For anemia, Grade 3 corresponds to Hgb<8.0 g/dL; <4.9 mmol/L; <80 g/L, where a transfusion is indicated. For thrombocytopenia (decreased platelet count), Grade 3 corresponds to <50,000-25,000/mm$^3$; <50.0-25.0×10$^9$/L. The sustained-release data was evaluated for patients over the course of 16 weeks. Mean duration of exposure to ruxolitinib in the COMFORT-I was approximately 242 days. Typically, the majority of hematologic adverse events occur within the first few months of therapy as observed in the COMFORT-I study.

TABLE 6b

Treatment-Related Haematologic Adverse Events By Organ Class, Preferred Term, and Maximum Severity in the Sustained-Release Study (First 16 Weeks)*

| MedDRA System Organ Class/MedDRA Preferred Term | Ruxolitinib (N = 41) | | | | |
|---|---|---|---|---|---|
| | Mi | Mo | Se | LT | Any |
| Number (%) of Subjects With Any Adverse Events | 16 | 9 | 7 | 0 | 32 (78.0) |
| Blood and lymphatic system disorders | 3 | 4 | 1 | 0 | 8 (19.5) |
| Anaemia | 0 | 2 | 0 | 0 | 2 (4.9) |
| Thrombocytopenia | 3 | 2 | 1 | 0 | 6 (14.6) |

*Mi (mild), Mo (moderate), Se (severe), LT (life threatening)

TABLE 6c

Treatment-Related Adverse Events By MedDRA System Organ Class, Preferred Term, and Maximum Severity in COMFORT I*

| MedDRA System Organ Class/ MedDRA Preferred Term | Ruxolitinib (N = 155) | | | | | | Placebo (N = 151) | | | | | |
|---|---|---|---|---|---|---|---|---|---|---|---|---|
| | Mi | Mo | Se | LT | FT | Any | Mi | Mo | Se | LT | FT | Any |
| Number (%) of Subjects With Any Adverse Events | 20 | 58 | 55 | 9 | 9 | 151 (97.4) | 23 | 58 | 53 | 4 | 10 | 148 (98.0) |
| Blood and lymphatic system disorders | 20 | 28 | 27 | 10 | 0 | 85 (54.8) | 18 | 21 | 15 | 2 | 0 | 56 (37.1) |
| Anaemia | 4 | 20 | 16 | 8 | 0 | 48 (31.0) | 4 | 10 | 7 | 0 | 0 | 21 (13.9) |
| Thrombocytopenia | 21 | 19 | 11 | 2 | 0 | 53 (34.2) | 6 | 5 | 2 | 1 | 0 | 14 (9.3) |

*Mi (mild), Mo (moderate), Se (severe), LT (life threatening), FT (fatal)

As can be seen from the data in Table 6a, adverse events relating to anemia, thrombocytopenia, neutropenia, and all events that were considered Grade 3 or higher occurred less frequently in the sustained-release study compared with the COMFORT-I immediate-release study.

TABLE 6a

Percent of Patients with Selected Grade 3 or Higher Adverse Events

| Adverse Event | SR Study | COMFORT I Ruxolitinib | COMFORT I Placebo |
|---|---|---|---|
| All ≥ Grade 3 Adverse Events | 17.1% | 47.1% | 44.4% |
| Anemia | 0% | 15.5% | 4.6% |
| Thrombocytopenia | 2.4% | 8.4% | 2.0% |
| Neutropenia | 0% | 1.3% | 0.7% |

The occurrence of blood-related adverse events are further compared in Tables 6b and 6c which report the number and percentage of patients in the studies exhibiting certain reactions including anemia and thrombocytopenia. The sustained-release data was evaluated for patients over the course of 16 weeks. Mean duration of exposure to ruxolitinib in the COMFORT-I study was approximately 242 days. The vast majority of hematologic adverse events occur within the first few months of therapy as observed in the COMFORT-I study. As can be seen from the data in the tables, the number and percentage of patients exhibiting blood-related adverse events is lower in the sustained-release study. Additionally, the severity of the adverse events is lesser in the sustained-release study.

Comparative Example A

COMFORT I Clinical Trial—Immediate Release Formulation

A Phase 3 clinical trial was completed showing efficacy of ruxolitinib in myelofibrosis patients. In this double-blind trial, patients with intermediate-2 or high risk myelofibrosis were randomly assigned to twice-daily oral, immediate-release (see Example 1) ruxolitinib (155 patients) or placebo (154 patients). The starting dose of ruxolitinib depended on the baseline platelet count: 15 mg twice daily for a platelet count of 100×109 to 200×109 per liter and 20 mg twice daily for a count that exceeded 200×109 per liter. The dose was adjusted for lack of efficacy or excess toxicity. The primary end point was the proportion of patients with a reduction in spleen volume of 35% or more at 24 weeks, assessed by means of magnetic resonance imaging. Secondary end points included the durability of response, changes in symptom burden (assessed by the total symptom score), and overall survival.

The proportion of patients with a reduction of 35% or more in spleen volume at week 24 (primary end point) was 41.9% in the ruxolitinib group as compared with 0.7% in the placebo group. The proportion of patients with a reduction of 50% or more in the total symptom score from baseline to week 24, a pre-specified secondary end point, was significantly higher in the ruxolitinib group than in the placebo group (45.9% vs. 5.3%; odds ratio, 15.3; 95% CI, 6.9 to 33.7; P<0.001).

The study showed that ruxolitinib was associated with reductions in splenomegaly and symptoms that are prominent manifestations of myelofibrosis and appeared to be associated with an improvement in overall survival. Additionally, the most common toxic effects of anemia and thrombocytopenia were generally managed with dose modification. Details regarding this study are provided in Verstovsek, S., et al. "A double-blind, placebo-controlled trial of ruxolitinib for myelofibrosis," N. Eng. J. Med., 2012, Mar. 1:366(9):799-807, which is incorporated herein by reference in its entirety.

Comparative Example B

COMFORT II Clinical Trial—Immediate Release Formulation

A Phase 3 clinical trial was completed showing the superiority of ruxolitinib treatment in myelofibrosis patients compared with best available therapy. Continuous ruxolitinib therapy, as compared with the best available therapy, was associated with marked and durable reductions in splenomegaly and disease-related symptoms, improvements in role functioning and quality of life, and modest toxic effects.

Myelofibrosis patients were randomly assigned, in a 2:1 ratio, to receive ruxolitinib or the best available therapy, which included any commercially available agents (as monotherapy or in combination) or no therapy at all and which could be changed during the treatment phase. The starting dose of ruxolitinib tablets was 15 mg twice daily of an immediate release formulation (See Example 1) if the baseline platelet count was 200×109 per liter or less and 20 mg orally twice daily if the baseline platelet count was greater than 200×109 per liter.

The primary end point was a reduction of 35% or more in spleen volume from baseline at week 48. At week 48, most of the patients in the ruxolitinib group had a reduction in spleen volume. Only patients in the ruxolitinib group met the criterion for the primary end point, at least a 35% reduction in spleen volume from baseline at 48 weeks (28%, vs. 0% in the group receiving the best available therapy; P<0.001). Patients in the ruxolitinib group, as compared with patients receiving the best available therapy, had improved quality of life and role functioning. At week 48, patients receiving ruxolitinib had marked reductions in myelofibrosis associated symptoms, including appetite loss, dyspnea, fatigue, insomnia, and pain, whereas patients receiving the best available therapy had worsening symptoms.

Thrombocytopenia and anemia occurred more frequently in the patients receiving ruxolitinib than in those receiving the best available therapy, but these events were generally manageable with dose modifications, transfusions of packed red cells, or both. Additional details of the study are provided in Harrison, C. et al., "JAK inhibition with ruxolitinib versus best available therapy for myelofibrosis," N. Eng. J. Med., 2012, Mar. 1; 366(9):787-98 which is incorporated herein by reference in its entirety.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. An oral sustained-release dosage form comprising: ruxolitinib phosphate, and
from about 10% to about 30% by weight of a sustained-release matrix former, which is hydroxypropyl methylcellulose,
wherein said ruxolitinib phosphate is present in said dosage form in an amount of 10 to 60 mg on a free base basis;
wherein the dosage form is suitable for oral administration; and
wherein administration of the dosage form to a human results in a ratio of mean peak plasma concentration ($C_{max}$) to mean 12-hour plasma concentration ($C_{12h}$) of ruxolitinib of 10 or less.

2. The oral sustained-release dosage form of claim 1, wherein administration of the dosage form to a human results in a mean peak plasma concentration ($C_{max}$) of ruxolitinib of 700 nM or less.

3. The oral sustained-release dosage form of claim 1, wherein administration of the dosage form to a human results in a mean peak plasma concentration ($C_{max}$) of ruxolitinib of 200 to 700 nM.

4. The oral sustained-release dosage form of claim 1, wherein administration of the dosage form to a human results in a mean peak plasma concentration ($C_{max}$) of ruxolitinib of 300 to 400 nM.

5. The oral sustained-release dosage form of claim 1, wherein administration of the dosage form to a human state results in a mean time to peak plasma concentration ($T_{max}$) of ruxolitinib of 1.5 hours or more.

6. The oral sustained-release dosage form of claim 1, wherein administration of the dosage form to a human results in a mean time to peak plasma concentration ($T_{max}$) of ruxolitinib of 1.5 hours to 5 hours.

7. The oral sustained-release dosage form of claim 1, wherein administration of the dosage form to a human results in a ratio of mean peak plasma concentration ($C_{max}$) to mean 12-hour plasma concentration ($C_{12h}$) of ruxolitinib of 4 or less.

8. The oral sustained-release dosage form of claim 1, wherein administration of the dosage form to a human results in a mean half-life ($t_{1/2}$) of from 4 hours to 8 hours.

9. The oral sustained-release dosage form of claim 1, wherein administration of a single dose of the dosage form to a human results in mean bioavailability ($AUC_{0-\infty}$) of ruxolitinib of 3000 to 4000 nM*h.

10. The oral sustained-release dosage form of claim 1, wherein administration of a single dose of the dosage form to a human results in mean bioavailability ($AUC_{0-\infty}$) of ruxolitinib of 3100 to 3800 nM*h.

11. The oral sustained-release dosage form of claim 1, which is in the form of a tablet or capsule.

12. The oral sustained-release dosage form of claim 1, wherein administration to a human results in a ruxolitinib plasma level of 75 to 500 nM for 8 hours.

13. The oral sustained-release dosage form of claim 1, wherein administration to a human results in a ruxolitinib plasma level of 75 to 500 nM for 12 hours.

14. The oral sustained-release dosage form of claim 1, wherein administration of said dosage form to a human once-daily for 16 weeks results in a mean decrease in mean platelet count from baseline of no more than 100×109/L.

15. The oral sustained-release dosage form of claim 14, wherein administration of said dosage form to a human once-daily for 16 weeks results in a mean decrease in mean platelet count from baseline of no more than 80×109/L.

16. The oral sustained-release dosage form of claim 14, wherein administration of said dosage form to a human once-daily for 16 weeks results in a mean decrease in mean platelet count from baseline of no more than 60×109/L.

17. The oral sustained-release dosage form of claim 14, wherein administration of said dosage form to a human once-daily for 16 weeks results in a mean decrease in mean platelet count from baseline of no more than 40×109/L.

18. The oral sustained-release dosage form of claim 1, wherein administration of said dosage form to a human once-daily for 16 weeks results in a mean decrease in mean hemoglobin from baseline of no more than 15 g/L.

19. The oral sustained-release dosage form of claim 18, wherein administration of said dosage form to a human once-daily for at least 16 weeks results in a mean decrease in mean hemoglobin from baseline of no more than 10 g/L.

20. The oral sustained-release dosage form of claim 18, wherein administration of said dosage form to a human once-daily for 16 weeks results in a mean decrease in mean hemoglobin from baseline of no more than 8 g/L.

21. The oral sustained-release dosage form of claim 18, wherein administration of said dosage form to a human once-daily for 16 weeks results in a mean decrease in mean hemoglobin from baseline of no more than 6 g/L.

22. The oral sustained-release dosage form of claim 1, wherein said ruxolitinib, or pharmaceutically acceptable salt thereof, is present in the dosage form in an amount of 10 mg on a free base basis.

23. The oral sustained-release dosage form of claim 1, wherein said ruxolitinib, or pharmaceutically acceptable salt thereof, is present in the dosage form in an amount of 12.5 mg on a free base basis.

24. The oral sustained-release dosage form of claim 1, wherein said ruxolitinib, or pharmaceutically acceptable salt thereof, is present in the dosage form in an amount of 20 mg on a free base basis.

25. The oral sustained-release dosage form of claim 1, wherein said ruxolitinib, or pharmaceutically acceptable salt thereof, is present in the dosage form in an amount of 30 mg on a free base basis.

26. The oral sustained-release dosage form of claim 1, wherein said ruxolitinib, or pharmaceutically acceptable salt thereof, is present in the dosage form in an amount of 37.5 mg on a free base basis.

27. The oral sustained-release dosage form of claim 1, wherein said ruxolitinib, or pharmaceutically acceptable salt thereof, is present in the dosage form in an amount of 40 mg on a free base basis.

28. The oral sustained-release dosage form of claim 1, wherein said ruxolitinib, or pharmaceutically acceptable salt thereof, is present in the dosage form in an amount of 50 mg on a free base basis.

29. The oral sustained-release dosage form of claim 1, wherein said ruxolitinib, or pharmaceutically acceptable salt thereof, is present in the dosage form in an amount of 60 mg on a free base basis.

30. The oral sustained-release dosage form of claim 1, wherein administration of the dosage form to a human results in a ratio of mean peak plasma concentration ($C_{max}$) to mean 12-hour plasma concentration ($C_{12h}$) of ruxolitinib of 6 or less.

31. The oral sustained-release dosage form of claim 1, wherein administration of the dosage form to a human results in a ratio of mean peak plasma concentration ($C_{max}$) to mean 12-hour plasma concentration ($C_{12h}$) of ruxolitinib of 5 or less.

32. The oral sustained-release dosage form of claim 1, wherein administration of the dosage form to a human results in a ratio of mean peak plasma concentration ($C_{max}$) to mean 12-hour plasma concentration ($C_{12h}$) of ruxolitinib of 1 to 10.

33. The oral sustained-release dosage form of claim 1, wherein administration of the dosage form to a human results in a ratio of mean peak plasma concentration ($C_{max}$) to mean 12-hour plasma concentration ($C_{12h}$) of ruxolitinib of 2 to 7.

34. An oral sustained-release oral dosage form, comprising:
   ruxolitinib phosphate, and
   from 10% to 30% by weight of a sustained-release matrix former, which is hydroxypropyl methylcellulose,
   wherein said ruxolitinib phosphate is present in said dosage form in an amount of 10 to 60 mg on a free base basis;
   wherein the dosage form is suitable for oral administration;
   wherein administration of said dosage form to a human results in a ratio of mean peak plasma concentration ($C_{max}$) to mean 12-hour plasma concentration ($C_{12h}$) of ruxolitinib of 10 or less; and
   wherein administration of the dosage form to a human results in a mean half-life ($t_{1/2}$) of from 3.5 hours to 11 hours.

35. The oral sustained-release dosage form of claim 34, wherein administration of the dosage form to a human results in a ratio of mean peak plasma concentration ($C_{max}$) to mean 12-hour plasma concentration ($C_{12h}$) of ruxolitinib of 2 to 7.

36. The oral sustained-release dosage form of claim 35, wherein administration of the dosage form to a human patient results in a reduction in thrombocytopenia or anemia relative to an immediate-release dosing regimen.

* * * * *

UNITED STATES PATENT AND TRADEMARK OFFICE
CERTIFICATE OF CORRECTION

Page 1 of 2

PATENT NO. : 10,874,616 B2
APPLICATION NO. : 16/190883
DATED : December 29, 2020
INVENTOR(S) : Yong Ni et al.

It is certified that error appears in the above-identified patent and that said Letters Patent is hereby corrected as shown below:

On the Title Page

Column 2, Item (56), under Other Publications Line 13, delete "Australian" and insert -- Argentina --.

In the Claims

Column 26, Line 23, Claim 5, after "human" delete "state.".

Column 26, Line 57, Claim 14, delete "109/L." and insert -- $10^9$/L. --.

Column 26, Line 61, Claim 15, delete "109/L." and insert -- $10^9$/L. --.

Column 26, Line 65, Claim 16, delete "109/L." and insert -- $10^9$/L. --.

Column 27, Line 2, Claim 17, delete "109/L." and insert -- $10^9$/L. --.

Column 27, Line 19, Claim 22, delete "ruxolitinib, or pharmaceutically acceptable salt thereof" and insert -- ruxolitinib phosphate --.

Column 27, Line 23, Claim 23, delete "ruxolitinib, or pharmaceutically acceptable salt thereof" and insert -- ruxolitinib phosphate --.

Column 27, Line 27, Claim 24, delete "ruxolitinib, or pharmaceutically acceptable salt thereof" and insert -- ruxolitinib phosphate --.

Column 27, Line 31, Claim 25, delete "ruxolitinib, or pharmaceutically acceptable salt thereof" and insert -- ruxolitinib phosphate --.

Column 27, Line 35, Claim 26, delete "ruxolitinib, or pharmaceutically acceptable salt thereof" and insert -- ruxolitinib phosphate --.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,874,616 B2

Column 27, Line 39, Claim 27, delete "ruxolitinib, or pharmaceutically acceptable salt thereof" and insert -- ruxolitinib phosphate --.

Column 27, Line 43, Claim 28, delete "ruxolitinib, or pharmaceutically acceptable salt thereof" and insert -- ruxolitinib phosphate --.

Column 27, Line 47, Claim 29, delete "ruxolitinib, or pharmaceutically acceptable salt thereof" and insert -- ruxolitinib phosphate --.